US009676819B2

(12) United States Patent
Jackson et al.

(10) Patent No.: US 9,676,819 B2
(45) Date of Patent: Jun. 13, 2017

(54) IMMUNOSTIMULATORY METHOD

(75) Inventors: David Charles Jackson, Carlton (AU); Amabel Tan, Carlton (AU); Weiguang Zeng, Carlton (AU)

(73) Assignee: INNAVAC PTY LTD (AU)

( * ) Notice: Subject to any disclaimer, the term of this patent is extended or adjusted under 35 U.S.C. 154(b) by 18 days.

(21) Appl. No.: 13/825,679

(22) PCT Filed: Sep. 22, 2011

(86) PCT No.: PCT/AU2011/001225
§ 371 (c)(1),
(2), (4) Date: May 15, 2013

(87) PCT Pub. No.: WO2012/037612
PCT Pub. Date: Mar. 29, 2012

(65) Prior Publication Data
US 2013/0230544 A1     Sep. 5, 2013

(30) Foreign Application Priority Data

Sep. 22, 2010 (AU) ................................ 2010904284
Jun. 20, 2011 (AU) ................................ 2011902408

(51) Int. Cl.
| C07K 7/06 | (2006.01) |
| A61K 38/06 | (2006.01) |
| A61K 38/07 | (2006.01) |
| A61K 38/08 | (2006.01) |
| A61K 38/39 | (2006.01) |
| A61K 39/39 | (2006.01) |

(52) U.S. Cl.
CPC .............. *C07K 7/06* (2013.01); *A61K 38/06* (2013.01); *A61K 38/07* (2013.01); *A61K 38/08* (2013.01); *A61K 39/39* (2013.01)

(58) Field of Classification Search
None
See application file for complete search history.

(56) References Cited

U.S. PATENT DOCUMENTS

| 8,986,700 B2 | 3/2015 | Jackson et al. |
| 9,089,508 B2 | 7/2015 | Jackson et al. |
| 2004/0191270 A1 | 9/2004 | Drane et al. |
| 2007/0066534 A1 | 3/2007 | Jackson et al. |
| 2008/0069831 A1 | 3/2008 | Duke et al. |
| 2008/0069832 A1 | 3/2008 | Chomez et al. |
| 2010/0310595 A1* | 12/2010 | Jackson et al. ............ 424/193.1 |
| 2011/0280899 A1 | 11/2011 | Jackson et al. |

FOREIGN PATENT DOCUMENTS

| EP | 1 550 458 | 7/2005 |
| EP | 1 666 056 A1 | 6/2006 |
| WO | WO 01/37869 | 5/2001 |
| WO | WO 2004/014956 | 2/2004 |
| WO | WO 2004/014957 | 2/2004 |
| WO | WO 2005/112991 | 12/2005 |
| WO | WO 2006/069262 | 6/2006 |
| WO | WO 2006/084319 | 8/2006 |
| WO | WO 2006/091591 | 8/2006 |
| WO | WO 2008/085549 | 7/2008 |
| WO | WO/2009/046498 | * 4/2009 |
| WO | WO 2009/155332 | 12/2009 |
| WO | WO 2010/028246 | 3/2010 |
| WO | WO 2010/093436 | 8/2010 |
| WO | WO 2010/111485 | 9/2010 |
| WO | WO 2011/080259 | 7/2011 |

OTHER PUBLICATIONS

Jackson et al. A totally synthetic vaccine of generic structure that targets Toll-like receptor 2 on dendritic cells and promotes antibody or cytotoxic T cell responses. Proc Natl Acad Sci U S A. Oct. 26, 2004;101(43):15440-5. Epub Oct. 15, 2004.*
Basto et al. Targeting TLR2 for Vaccine Development. Journal of Immunology Research. vol. 2014, Article ID 619410, 22 pages.*
Reppe et al. Immunostimulation with macrophage-activating lipopeptide-2 increased survival in murine pneumonia. Am J Respir Cell Mol Biol. Apr. 2009;40(4):474-81. Epub Oct. 17, 2008.*
TLR2-Wikipedia, the free encyclopedia. undated.*
Cluff et al. Synthetic Toll-Like Receptor 4 Agonists Stimulate Innate Resistance to Infectious Challenge . Infection and Immunity, 2005, 73: 3044-3052.*
Archer et al. MyD88-dependent responses involving toll-like receptor 2 are important for protection and clearance of Legionella pneumophila in a mouse model of Legionnaires' disease. Infect Immun. Jun. 2006;74(6):3325-33.*
LiCalsi et al. Dry powder inhalation as a potential delivery method for vaccines. Vaccine. Mar. 26, 1999;17(13-14):1796-803.*
Alphs, HH et al., "Protection against heterologous human papillomavirus challenge by a synthetic lipopeptide vaccine containing a broadly cross-neutralizing epitope of L2" *Proceedings of the National Academy of Science*, 2008, 105(15):5850-5855.
Rose, WA et al.,"FSL-1, a bacterial-derived toll-like receptor 2/6 agonist, enhances resistance to experimental HSV-2 infection" *Virology Journal*, 2009, 6:195-205.
Voss, S et al., "The activity of lipopeptide TLR2 agonists critically depends on the presence of solubilizers" *European Journal of Immunology*, 2007, 37:3489-3498.
Ghielmetti, M. et al. "Synthetic bacterial lipopeptide analogs facilitate naïve CD4+ T cell differentiation and enhance antigen-specific HLA-II-restricted responses" *Eur. J. Immunol.*, 2005, 35:2434-2442.

(Continued)

*Primary Examiner* — Nianxiang (Nick) Zou
(74) *Attorney, Agent, or Firm* — Saliwanchik, Lloyd & Eisenschenk

(57) ABSTRACT

This invention relates to a method for treating or preventing a disease by raising an innate immune response in a subject, the method comprising administering to the subject an effective amount of a composition comprising a TLR2 moiety in solution, wherein the TLR2 moiety comprises a TLR2 agonist and wherein the disease is not treated or prevented by a humoral or cellular immune response directed against the TLR2 moiety.

28 Claims, 16 Drawing Sheets

(56) References Cited

OTHER PUBLICATIONS

Meng, G. et al. "Cellular recognition of tri-/di-palmitoylated peptides is independent from a domain encompassing the N-terminal seven leucine-rich repeat (LRR)/LRR-like motifs of TLR2" *J. Biol. Chem.*, 2003, 278(41):39822-39829.

Azuma, M. et al. "The peptide sequence of diacyl lipopeptides determines dendritic cell TLR2-mediated NK activation" *PLoS One*, 2010, 5(9):e12550.

Fuse, E. et al. "Role of Toll-like receptor 2 in recognition of *Legionella pneumophila* in a murine pneumonia model" *J. Med. Microbiol.*, 2007, 56:305-312.

Heuking, S. et al. "Stimulation of human macrophages (THP-1) using Toll-like receptor-2 (TLR-2) agonist decorated nanocarriers" *J. Drug Targeting*, 2009, 17(8):662-670.

Hoffman, P. et al. "Induction of tumor cytotoxicity in murine bone marrow-derived macrophages by two synthetic lipopeptide analogues" *Biol. Chem. Hoppe-Seyler*, 1989, 370:575-582.

Martinez, J. et al. "Direct TLR2 signaling is critical for NK cell activation and function in response to vaccinia viral infection" *PLoS Pathogens*, 2010, 6(3):e1000811.

Mühlradt, P. et al. "Structure and specific activity of macrophage-stimulating lipopeptides from *Mycoplasma hyorhinis*" *Infection and Immunity*, 1998, 66(10):4804-4810.

Seifert, R. et al. "Activation of superoxide formation and lysozyme release in human neutrophils by the synthetic lipopeptide Pam$_3$Cys-Ser-(Lys)$_4$" *Biochem. J.*, 1990, 267:795-802.

Belz, G.T., et al., "A Previously Unrecognized H-2D$^b$-Restricted Peptide Prominent in the Primary Influenza A Virus-Specific CD8$^+$ T-Cell Response Is Much Less Apparent following Secondary Challenge," *Journal of Virology*, Apr. 2000, vol. 74, No. 8, pp. 3486-3493.

Bodmer, H.C., et al., "Enhanced Recognition of a Modified Peptide Antigen by Cytotoxic T Cells Specific for Influenza Nucleoprotein," *Cell*, Jan. 29, 1988, vol. 52, pp. 253-258.

Cleret, A., et al., "Lung Dendritic Cells Rapidly Mediate Anthrax Spore Entry through the Pulmonary Route," *Journal of Immunology*, 2007, vol. 178, pp. 7994-8001.

Duggan, J.M., et al., "Synergistic Interactions of TLR2/6 and TLR9 Induce a High Level of Resistance to Lung Infection in Mice," *Journal of Immunology*, 2011, vol. 186, pp. 5916-5926.

Firat, H., et al., "H-2 class I knockout, HLA-A2.1-transgenic mice: a versatile animal model for preclinical evaluation of antitumor immunotherapeutic strategies," *Eur. J. Immunol.*, 1999, vol. 29, pp. 3112-3121.

Gianfrani, C., et al., "Human Memory CTL Response Specific for Influenza A Virus is Broad and Multispecific," *Human Immunology*, 2000, vol. 61, pp. 438-452.

Gonzalez-Juarrero, M., et al., "Dynamics of Macrophage Cell Populations During Murine Pulmonary Tuberculosis," *Journal of Immunology*, 2003, vol. 171, pp. 3128-3135.

Gotch, F., et al., "Cytotoxic T lymphocytes recognize a fragment of influenza virus matrix protein in association with HLA-A2," *Nature*, Apr. 30, 1987, vol. 326, pp. 881-882.

Jameson, J., et al., "Human CD8$^+$ and CD4$^+$ T Lymphocyte Memory to Influenza A Viruses of Swine and Avian Species," *Journal of Immunology*, 1999, vol. 162, pp. 7578-7583.

Landsman, L., et al., "Lung Macrophages Serve as Obligatory Intermediate between Blood Monocytes and Alveolar Macrophages," *Journal of Immunology*, 2007, vol. 179, pp. 3488-3494.

Pascolo, S., et al., "HLA-A2.1-restricted Education and Cytolytic Activity of CD8$^+$ T Lymphocytes from β2 Microglobulin (β2m) HLA-A2.1 Monochain Transgenic H-2D$^b$ β2m Double Knockout Mice," *J. Exp. Med.*, Jun. 16, 1997, vol. 185, No. 12, pp. 2043-2051.

Sherman, L.A., et al., "Extracellular Processing of Peptide Antigens That Bind Class I Major Histocompatibility Molecules," *J. Exp. Med.*, May 1992, vol. 175, pp. 1221-1226.

Tannock, G.A., et al., "Relative Immunogenicity of the Cold-Adapted Influenza Virus Ann Arbor/6/60 (A/AA/6/60-ca), Recombinants of A/AA/6/60-ca, and Parental Strains with Similar Surface Antigens," *Infection and Immunity*, Feb. 1984, vol. 43, No. 2, pp. 457-462.

Wallace, M.E., et al., "The Cytotoxic T-Cell Response to Herpes Simplex Virus Type 1 Infection of C57BL/6 Mice Is Almost Entirely Directed against a Single Immunodominant Determinant," *Journal of Virology*, Sep. 1999, vol. 73, No. 9, pp. 7619-7626.

Zeng, W., et al., "Characterisation of the antibody response to a totally synthetic immunocontraceptive peptide vaccine based on LHRH," *Vaccine*, 2005, vol. 23, pp. 4427-4435.

Zeng, W., et al., "Highly Immunogenic and Totally Synthetic Lipopeptides as Self-Adjuvanting Immunocontraceptive Vaccines," *Journal of Immunology*, 2002, vol. 169, pp. 4905-4912.

Deliyannis, G. et al. "Intranasal lipopeptide primes lung-resident memory CD8$^+$ T cells for longterm pulmonary protection against influenza," *European Journal of Immunology*, 2006, vol. 36, pp. 770-780.

Lau, Y.F. et al. "Lipid-containing mimetics of natural triggers of innate immunity as CTL-inducing influenza vaccines," *International Immunology*, 2006, vol. 18, No. 12, pp. 1801-1813.

Palma, C. et al. "The Toll-like Receptor 2/6 Ligand MALP-2 Reduces the Viability of *Mycobacterium tuberculosis* in Murine Macrophages," *The Open Microbiology Journal*, 2009, vol. 3, pp. 47-52.

Alexopoulou et al. "Recognition of double-stranded RNA and activation of NF-kappaB by Toll-like receptor 3" *Nature*, Oct. 18, 2001, 413(6857):732-8.

Amigorena, S. "Fcγ receptors and cross-presentation in dendritic cells" *J. Exp. Med.*, 2002, 195(1):F1-F3.

Andrä, J. et al. "Enhancement of endotoxin neutralization by coupling of a C12-alkyl chain to a lactoferricin-derived peptide" *Biochem. J.*, Jan. 1, 2005, 385(1):135-143.

Asea et al. "Novel signal transduction pathway utilized by extracellular HSP70: role of toll-like receptor (TLR) 2 and TLR4" *J Biol Chem*, Apr. 26, 2002, 277(17):15028-34.

Baz, A. et al. "Branched and linear lipopeptide vaccines have different effects on primary CD4$^+$ and CD8$^+$ T-cell activation but induce similar tumor-protective memory CD8$^+$ T-cell responses" *Vaccine*, 2008, 26:2570-2579.

Brown and Gordon "Immune recognition. A new receptor for beta-glucans" *Nature*, Sep. 6, 2001, 413(6851):36-7.

Bulut et al. "Chlamydial heat shock protein 60 activates macrophages and endothelial cells through Toll-like receptor 4 and MD2 in a MyD88-dependent pathway" *J Immunol*, 2002, 168(3):1435-40.

Chow et al. "Toll-like receptor-4 mediates lipopolysaccharide-induced signal transduction" *J Biol Chem*, Apr. 16, 1999, 274(16):10689-92.

Chua et al. "Dendritic cell acquisition of epitope cargo mediated by simple cationic peptide structures" *Peptides*, 2008, 29:881-890.

Chua et al. "Enhancing immunogenicity of HCV DNA vaccines by targeted delivery to dendritic cells" *Journal of Hepatology*, 2008, 48:S236, abstract No. 634.

Chua et al. "Soluble Proteins Induce Strong CD8$^+$ T Cell and Antibody Responses through Electrostatic Association with Simple Cationic or Anionic Lipopeptides That Target TLR2" *The Journal of Immunology*, 2011, 187:1692-1701.

Engering et al. "The mannose receptor functions as a high capacity and broad specificity antigen receptor in human dendritic cells" *Eur J Immunol*, Sep. 1997, 27(9):2417-25.

Farley, M.M. et al. "Lipopolysaccharide Structure Determines Ionic and Hydrophobic Binding of a Cationic Antimicrobial Neutrophil Granule Protein" *Infection and Immunity*, Jun. 1988, 56(6):1589-1592.

Feinberg et al. "Structural basis for selective recognition of oligosaccharides by DC-SIGN and DC-SIGNR" *Science*, Dec. 7, 2001, 294(5549):2163-6.

Frison et al. "Oligolysine-based oligosaccharide clusters: selective recognition and endocytosis by the mannose receptor and dendritic cell-specific intercellular adhesion molecule 3 (ICAM-3)-grabbing nonintegrin" *J Biol Chem*, Jun. 27, 2003, 278(26):23922-9.

(56) References Cited

OTHER PUBLICATIONS

Hayashi et al. "The innate immune response to bacterial flagellin is mediated by Toll-like receptor 5" *Nature*, Apr. 26, 2001, 410(6832):1099-103.
Heil et al. "Species-specific recognition of single-stranded RNA via toll-like receptor 7 and 8" *Science*, Mar. 5, 2004, 303(5663):1526-9.
Hemmi et al. "A Toll-like receptor recognizes bacterial DNA" *Nature*, Dec. 7, 2000, 408(6813):740-5.
Hemmi et al. "Small anti-viral compounds activate immune cells via the TLR7 MyD88-dependent signaling pathway" *Nat Immunol*, Feb. 2002, 3(2):196-200.
http://medical-dictionary.thefreedictionary.com/admixture, Aug. 26, 2016, pp. 1-3.
Ismaili, J. et al. "Monophosphoryl lipid A activates both human dendritic cells and T cells" *J. Immunol.*, 2002, 168:926-932.
Kery et al. "Ligand recognition by purified human mannose receptor" *Arch Biochem Biophys*, Oct. 1992, 298(1):49-55.
Metzger, J. et al. "Synthesis of novel immunologically active tripalmitoyl-S-glycerylcysteinyl lipopeptides as useful intermediates for immunogen preparations" *Int. J. Peptide Protein Res.*, 1991, 37:46-57.
Morr et al. "Differential recognition of structural details of bacterial lipopeptides by toll-like receptors" *Eur J Immunol*, Dec. 2002, 32(12):3337-47.
Okusawa et al. "Relationship between structures and biological activities of mycoplasmal diacylated lipopeptides and their recognition by toll-like receptors 2 and 6" *Infect Immun*, Mar. 2004, 72(3):1657-65.
Ozinsky et al. "The repertoire for pattern recognition of pathogens by the innate immune system is defined by cooperation between toll-like receptors" *Proc Natl Acad Sci USA*, Dec. 5, 2000, 97(25):13766-71.
Pina, D.G. et al. "Shiga toxin B-subunit sequential binding to its natural receptor in lipid membranes" *Biochimica et Biophysica Acta*, 2007, 1768:628-636.
Poltorak et al. "Defective LPS signaling in C3H/HeJ and C57BL/10ScCr mice: mutations in Tlr4 gene" *Science*, Dec. 11, 1998, 282(5396):2085-8.
Raffai, R. et al. "Binding of an antibody mimetic of the human low density lipoprotein receptor to apolipoprotein E is governed through electrostatic forces" *J. Biol. Chem.*, 2000, 275(10):7109-7116.
Raffai, R. et al. "Molecular characterization of two monoclonal antibodies specific for the LDL receptor-binding site of human apolipoprotein E" *J. Lipid Res.*, 1995, 36:1905-1918.
Schwandner et al. "Peptidoglycan- and lipoteichoic acid-induced cell activation is mediated by toll-like receptor 2" *J Biol Chem*, Jun. 18, 1999, 274(25):17406-9.
Stambach and Taylor "Characterization of carbohydrate recognition by langerin, a C-type lectin of Langerhans cells" *Glycobiology*, May 2003, 13(5):401-10.
Takeuchi et al. "Cutting edge: preferentially the R-stereoisomer of the mycoplasmal lipopeptide macrophage-activating lipopeptide-2 activates immune cells through a toll-like receptor 2- and MyD88-dependent signaling pathway" *J Immunol*, Jan. 15, 2000, 164(2):554-7.
Takeuchi et al. "Cutting edge: role of Toll-like receptor 1 in mediating immune response to microbial lipoproteins" *J Immunol*, Jul. 2002, 169(1):10-14.
Tansey, W. et al. "Synthesis and characterization of branched poly(L-glutamic acid) as a biodegradable drug carrier" *J. Controlled Release*, 2004, 94:39-51.
Tighe et al. "Conjugation of protein to immunostimulatory DNA results in a rapid, long-lasting and potent induction of cell-mediated and humoral immunity" *European Journal of Immunology*, 2000, 30:1939-1947.
Zeng et al. "Synthesis of a New Template with a Built-in Adjuvant and Its Use in Constructing Peptide Vaccine Candidates Through Polyoxime Chemistry" *Journal of Peptide Science*, 1996, 2:66-72.
Office Action dated Sep. 6, 2016, received in U.S. Appl. No. 14/602,778.

\* cited by examiner

IMMUNOSTIMULATORY METHOD

CROSS-REFERENCE TO RELATED APPLICATION

This application is the National Stage of International Application Number PCT/AU2011/001225, filed Sep. 22, 2011, the disclosure of which is incorporated herein by reference in its entirety, including all figures, tables and drawings.

TECHNICAL FIELD

The present invention relates to a novel method for eliciting an innate immune response in a subject involving the use of a TLR2 moiety comprising a TLR2 agonist.

BACKGROUND

Influenza A virus (IAV) infection causes up to 1 billion infections and 300,000-500,000 deaths annually and the global outbreak of the swine H1N1 in 2009 has highlighted the limited anti-viral options available to cope with a pandemic influenza. Although vaccines are available against the seasonal IAV epidemics, these vaccines induce antibodies against the ever-evolving neuraminidase and hemagglutinin surface proteins of IAV and therefore require annual re-formulation and administration. Moreover these vaccines are generally not effective against pandemic outbreaks caused by newly emergent viruses. An alternative is to target the conserved internal regions of IAV. However, the recent pandemic outbreak of a swine H1N1 Influenza A virus has led the quest to discover broadly protective vaccines and anti-viral options against pandemic influenza.

The present invention is concerned with the development of a novel approach to the treatment influenza as well as other infectious diseases and cancers.

SUMMARY OF THE INVENTION

In a first aspect of the present invention there is provided a method for treating or preventing a disease by raising an innate immune response in a subject, the method comprising administering to the subject an effective amount of a composition comprising a TLR2 moiety in solution, wherein the TLR2 moiety comprises a TLR2 agonist and wherein the disease is not treated or prevented by a humoral or cellular immune response directed against the TLR2 moiety.

In a second aspect of the present invention there is provided a method for treating or preventing a disease caused by an infectious agent, the method comprising administering to a subject in need thereof an effective amount of a composition comprising a TLR2 moiety in solution, wherein the TLR2 moiety comprises a TLR2 agonist and wherein the TLR2 moiety does not induce a specific cellular or humoral immune response directed against the infectious agent.

In a third aspect of the present invention there is provided a method for treating or preventing cancer by raising an innate immune response in a subject, the method comprising administering to the subject a therapeutically effective amount of a composition comprising a TLR2 moiety in solution, wherein the TLR2 moiety comprises a TLR2 agonist and wherein TLR2 moiety does not induce a specific cellular or humoral immune response directed against the cancer.

In a fourth aspect of the present invention there is provided a pharmaceutical composition comprising an effective amount of a TLR2 moiety in solution together with a pharmaceutically acceptable carrier or excipient for treating or preventing a disease by raising an innate immune response in a subject, wherein the TLR2 moiety comprises a TLR2 agonist and wherein the disease is not treated or prevented by a humoral or cellular immune response directed against the TLR2 moiety.

In a fifth aspect of the present invention there is provided use of an effective amount of a TLR2 moiety in solution for the manufacture of a medicament for treating or preventing a disease in a subject, wherein the TLR2 moiety comprises a TLR2 agonist, wherein the TLR2 agonist raises an innate immune response in the subject and wherein the disease is not treated or prevented by a humoral or cellular immune response directed against the TLR2 moiety.

Kaplan-Meier plot showing survival of C57BL/6 mice (left hand) and HHD mice (right hand) inoculated intranasally with saline, IAV-LP or non-IAV-LP (n=5/group) and challenged 7 days later with H1N1 PR8 virus. Lower panels: Changes in body weight following infection. Symbols indicate the mean and error bars indicate SEM. These results were reflected in an independent repeat of the experiment in both mouse strains.

Figure 5:
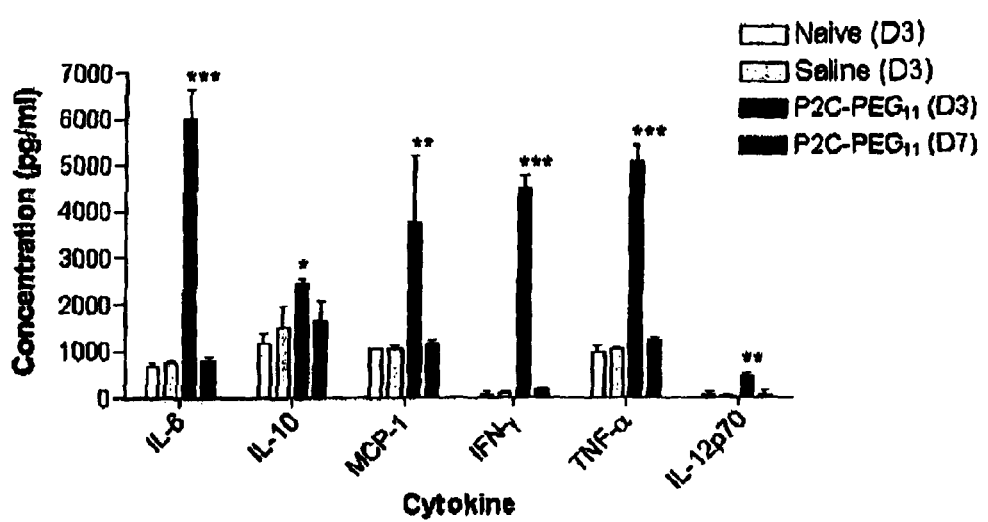

FIG. 5 shows Pam2Cys on the pulmonary cytokine environment. C57BL/6 mice were administered 20 nmol of Pam2Cys-PEG$_{11}$ (P2C-PEG$_{11}$) or 50 µl of saline (i.n) and the concentration of cytokines in the Bronchoalveolar lavage (BAL) fluid was determined at day 3 (D3) or 7 (D7) post-administration using a BD™ Cytometric Bead Array. Bars represent the mean response of each group (n=3) and error bars indicate the SD, *=P<0.05; P<0.01; *=P<0.001 vs. Saline and Naive groups (One-way ANOVA and post hoc Tukey's multiple comparison test).

Figure 6:
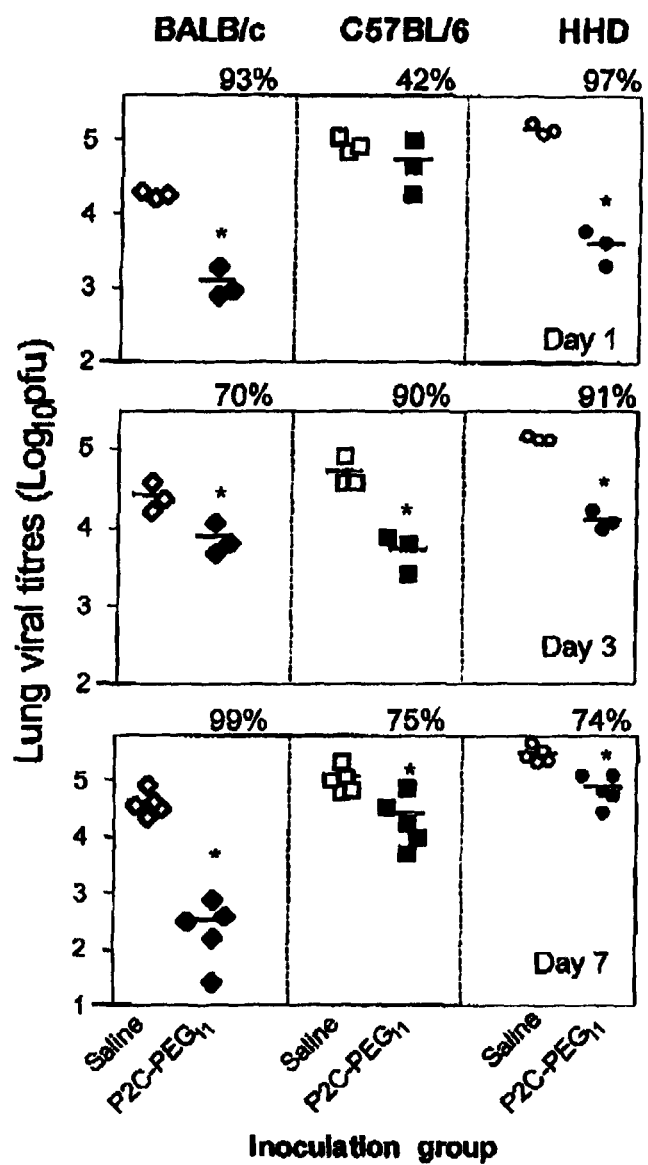

FIG. 6 shows that Pam2Cys mediates viral clearance. Mice were inoculated with saline or 20 nmol of Pam2Cys-PEG$_{11}$ and challenged 1 (upper panel), 3 (middle panel) or 7 (lower panel) days later with $10^{4.5}$ pfu of Mem71 (H3N1) virus (n=3-5/group). The viral titres were assessed at day 5 of infection in BALB/c ($\diamond$), C57BL/6 ($\square$) and HHD ($\bigcirc$) mice. Symbols represent the titre obtained from an individual mouse and the line indicates the mean virus titre of the group, *=P<0.05 vs Saline (unpaired student's t-test). The percentage of viral clearance relative to the saline group is indicated above the Pam2Cys response.

Figure 7:
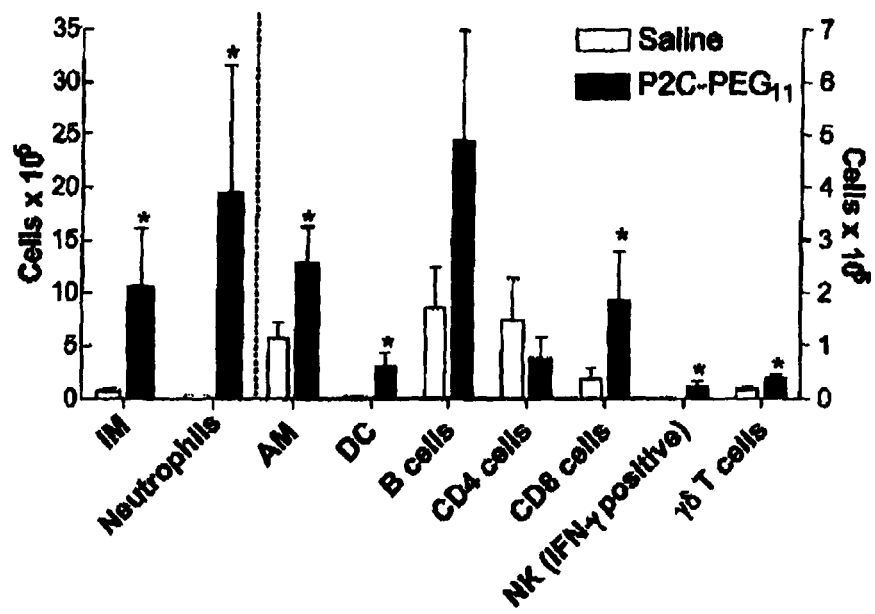

FIG. 7 shows that intranasal Pam2Cys administration expands cell subpopulations in the lung. C57BL/6 mice were administered 20 nmol of pegylated Pam2Cys (P2C-PEG$_{11}$) or 50 µl of saline (i.n) and the pulmonary cell populations were characterised 72 hr post-administration. Bars represent the mean response of each group (n=3) and error bars indicate the SD, *=P<0.05; vs. saline group (unpaired student's t-test).

Figure 8:
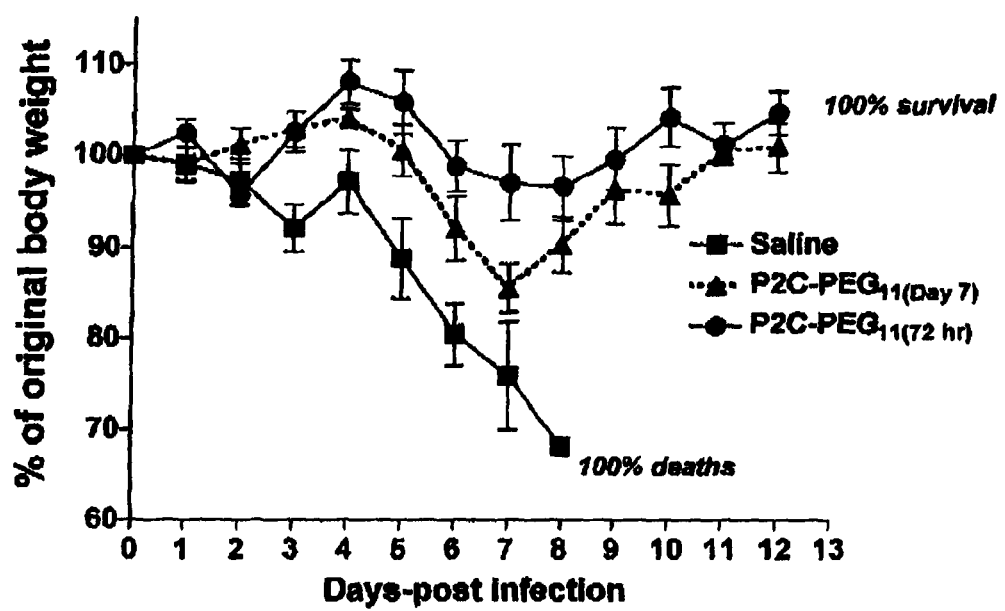

FIG. 8 shows that Pam2Cys protects against virulent IAV Infection. C57BL/6 mice were inoculated intranasally with saline or 20 nmol of pegylated Pam2Cys (P2C-PEG$_{11}$) (n=5/group) and challenged 7 days later with 200 pfu H1N1 PR8 virus. One group of mice received 20 nmol of P2C-PEG$_{11}$ and was challenged 72 hr later. The changes in body weight following infection are shown as a percentage of the original weight. Symbols indicate the mean and error bars indicate SEM. These results were reflected in an independent repeat of the experiment.

Figure 9:
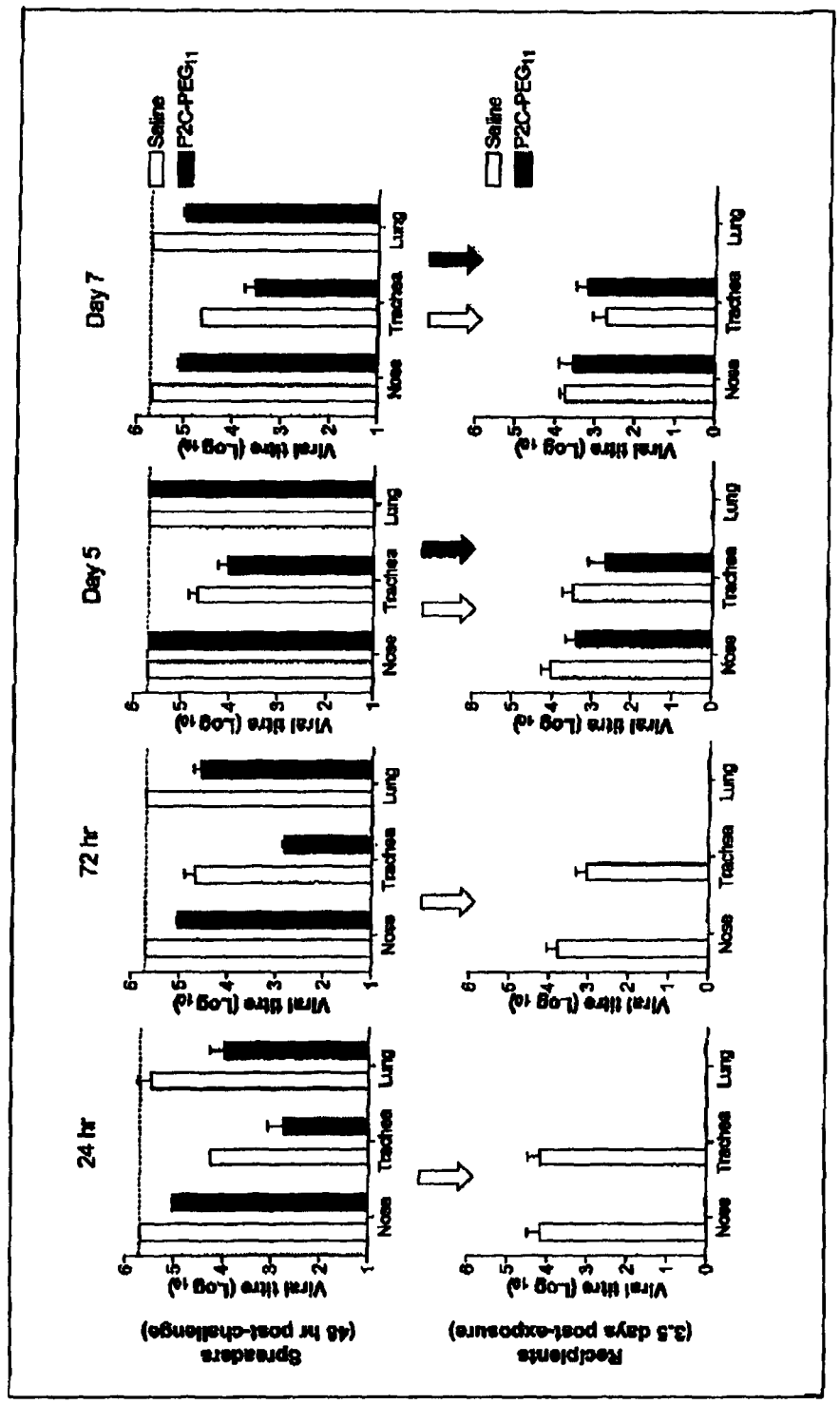

FIG. 9 shows that Pam2Cys prophylaxis reduces viral loads and contact transmission of influenza. BALB/c mice were inoculated with saline (white bars) or 20 nmol of pegylated Pam2Cys (P2C-PEG$_{11}$) (grey bars) and challenged 7 days, 5 days, 72 hr or 24 hr later with $10^{4.5}$ pfu of Udorn (H3N2) virus (n=2/group). These mice were designated as the spreader mice. Twenty-four hours following challenge, the spreader mice were co-housed with naïve recipient mice. Following 24 hr of co-housing, the spreader mice were removed and nasal turbinates, trachea and lungs were removed and viral titres were determined (upper panel). Organs from the recipient mice were harvested 3.5 days following exposure to the spreader mice and viral titres were assessed (lower panel). The white or grey arrows indicate successful contact-mediated transmission from the respective treatment group to the co-housed recipients.

Figure 10:
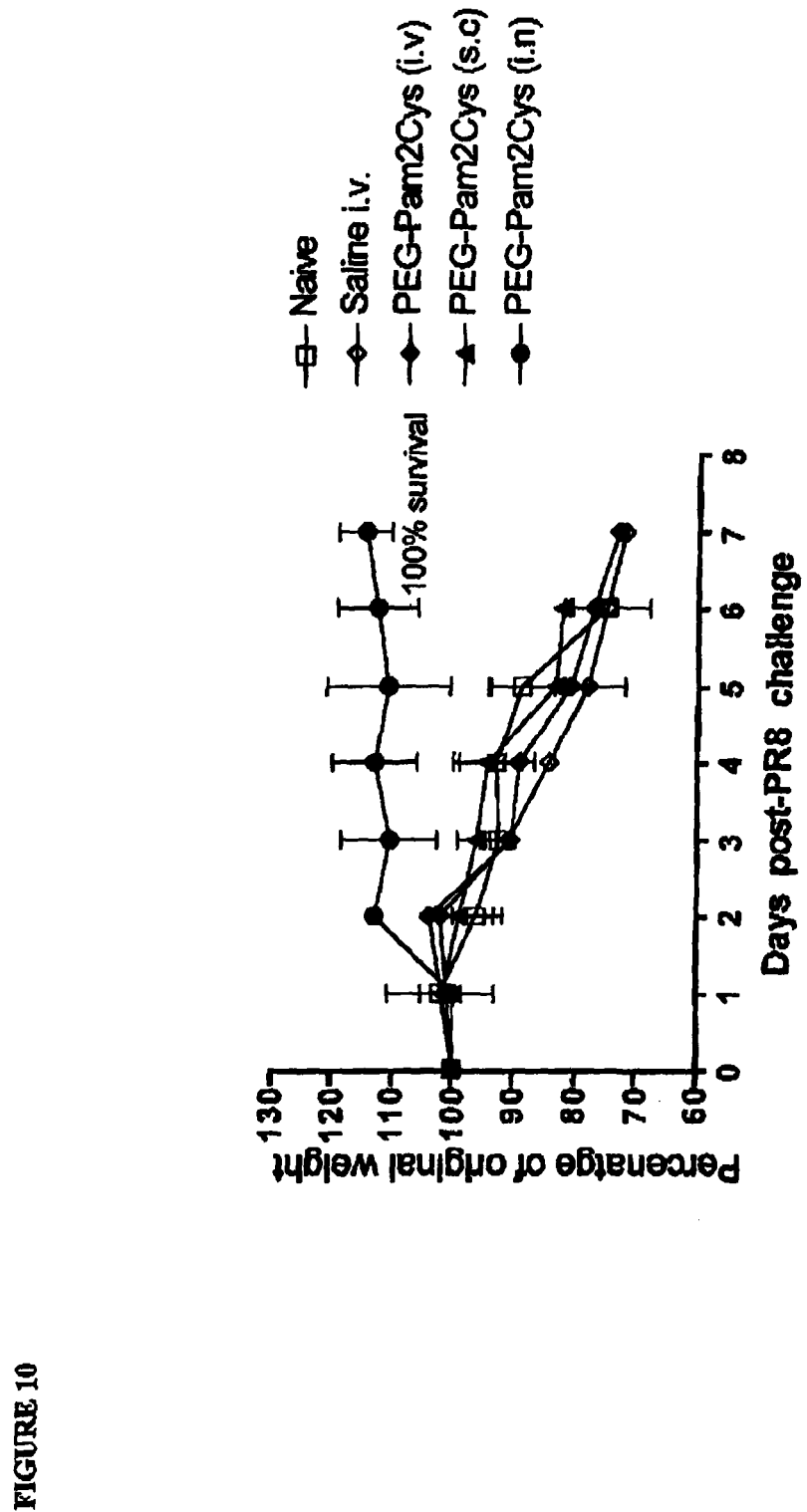

FIG. 10 shows that PEG-Pam2Cys protects in a single dose against IAV when delivered intranasally. Mice were prophylactically administered PEG-Pam2Cys (20 nmol) via the intranasal (i.n), subcutaneous (s.c) or intravenous (i.v) routes and 3 days later challenged with a lethal dose of PR8 virus. The mice were then monitored over an 8 day period post-PR8 for body weight and survival and culled at a humane end-point.

Figure 11:
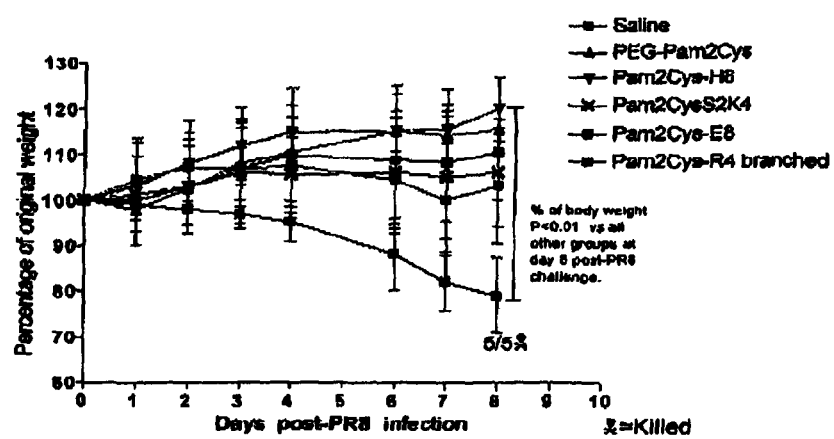
Figure 11:
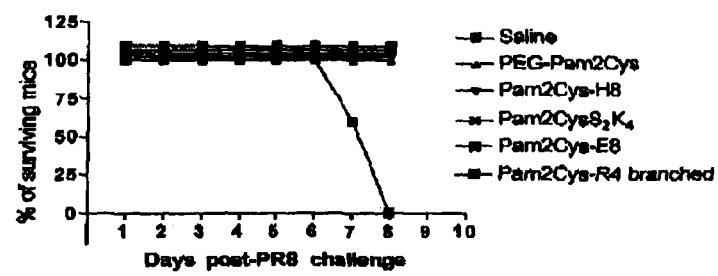

FIG. 11 shows that several Pam2Cys variants also confer protection against IAV challenge. Mice were prophylactically administered 20 nmol of various Pam2Cys containing constructs via the intranasal routes and 3 days later challenged with a lethal dose of PR8 virus. The mice were then monitored over an 8 day period post-PR8 for body weight (A) and survival (B). The reduction in body weight seen in the Saline group was statistically significant (P>0.01) when compared to each of the other treatment groups.

Figure 12:
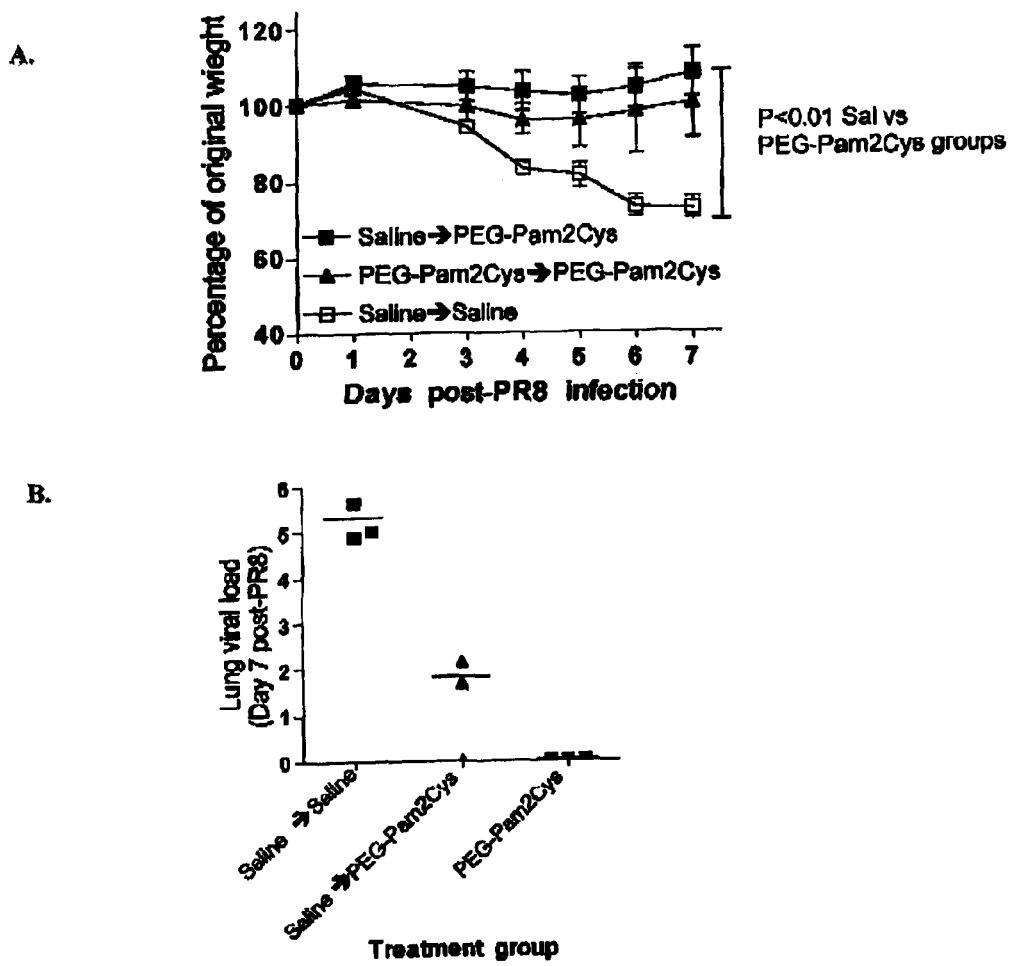

FIG. 12 shows that PEG-Pam2Cys is effective when given in a repeated dose. Balb/c mice were administered a single dose of PEG-Pam2Cys, or two doses of PEG-Pam2Cys three weeks apart and then challenged with PR8 three days after the second dose. The mice were then monitored over an 8 day period post-challenge for body weight and survival and culled on day 7 post-PR8 for assessment of lung viral load. The reduction in body weight seen in the Saline group was statistically significant (P<0.01) when compared to each of the other treatment groups (A). Viral loads in mice treated with PEG-Pam2Cys were substantially lower than in mice which received saline only (B).

Figure 13:
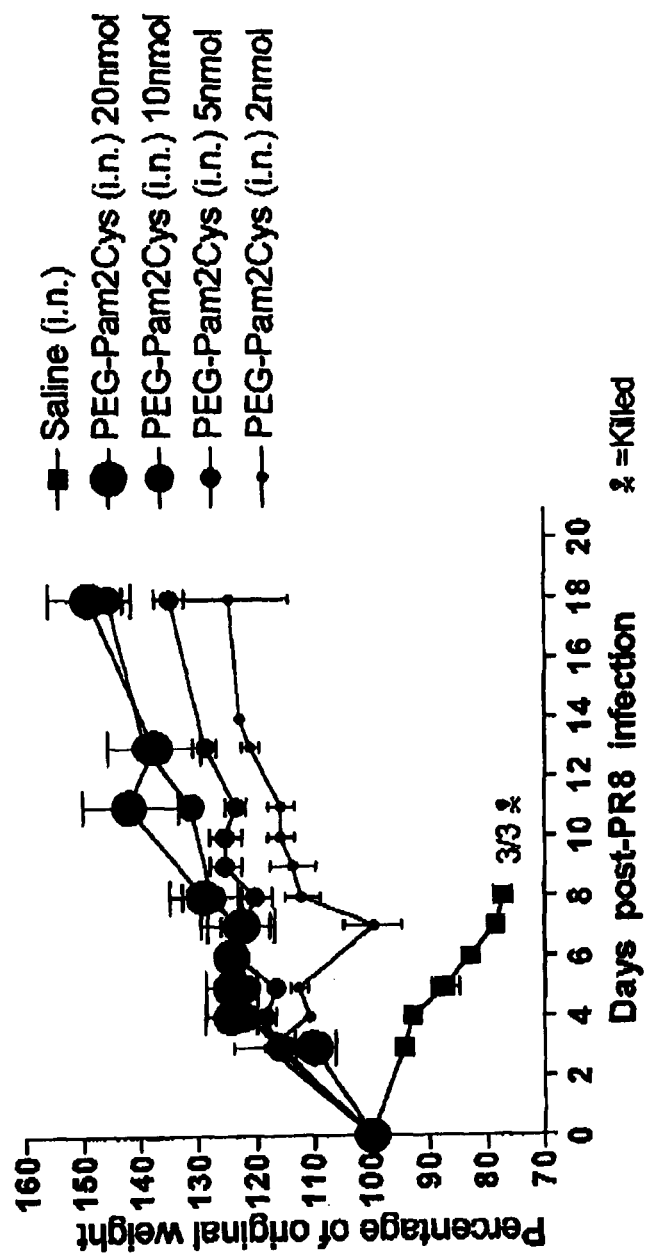

FIG. 13 shows that lower doses of PEG-Pam2Cys are also effective. Mice were prophylactically treated with lower doses of PEG-Pam2Cys at 2, 5 and 10 nmol (c.f. 20 nmol) and challenged 3 days later with a lethal dose of PR8 virus. The mice were monitored over an 18 day period post-challenge for change in body weight and survival and culled at a humane end-point. Mice within the Saline group did not survive beyond day 8 post-PR8 challenge.

Figure 14:
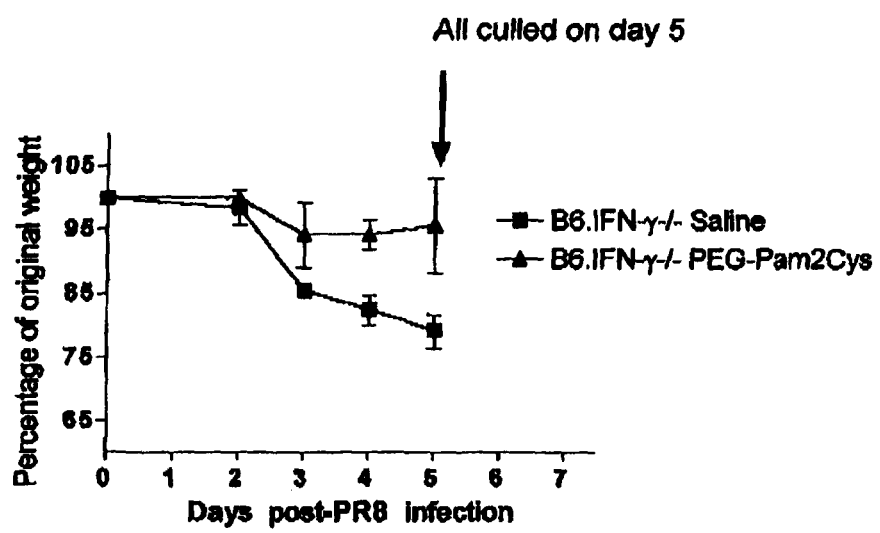
Figure 14:
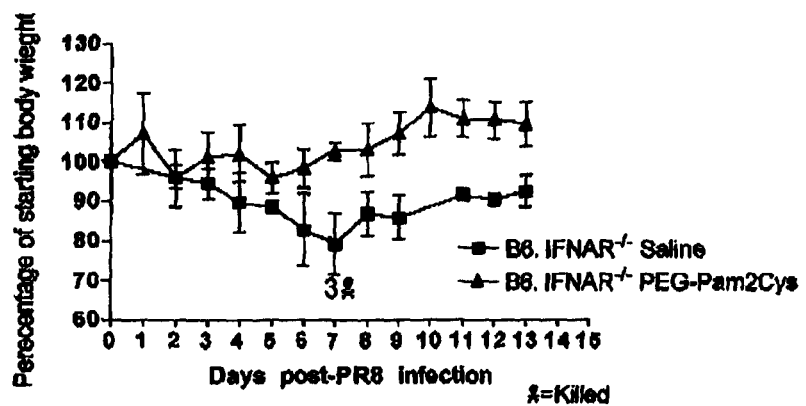

FIG. 14 shows that protection against IAV challenge is not dependant on IFN-γ or type 1 interferons (i.e. IFN-α). Mice deficient in IFN-γ (B6.IFN-γ-/-) (A) or the Type 1 interferon receptor (IFNAR-/-) (B) were prophylactically administered 20 nmol of PEG-Pam2Cys (i.n.) and 3 days later challenged with a lethal dose of PR8 virus. These mice were protected against the weight loss and lethality associated with PR8 infection. The B6.IFN-γ-/- cohort was culled on day 5, when the saline group reached a humane end point.

Figure 15:
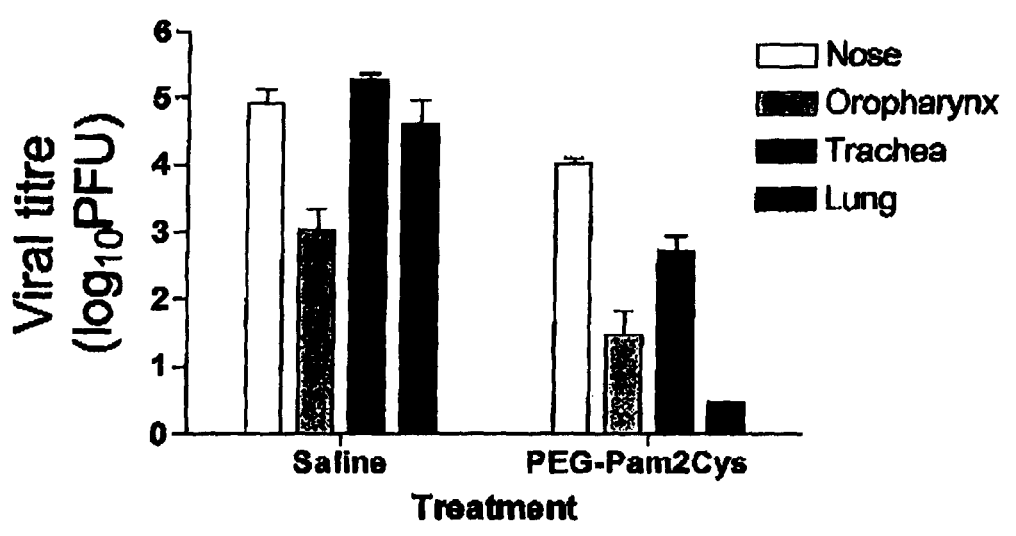

FIG. 15 shows that PEG-Pam2Cys is effective as a therapeutic agent. Balb/c mice were challenged i.n with $10^{4.5}$ PFU of Udorn virus and 4 hours later administered 20 nmol PEG-Pam2Cys (i.n.). Two days later, animals were culled and viral loads were determined in the nose, oropharynx, trachea and lung.

Figure 16:
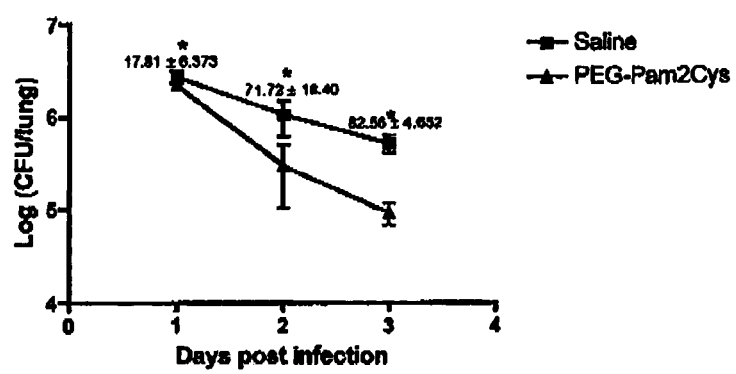
Figure 16:
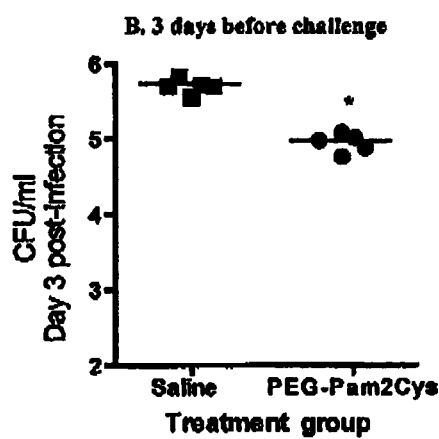
Figure 16:
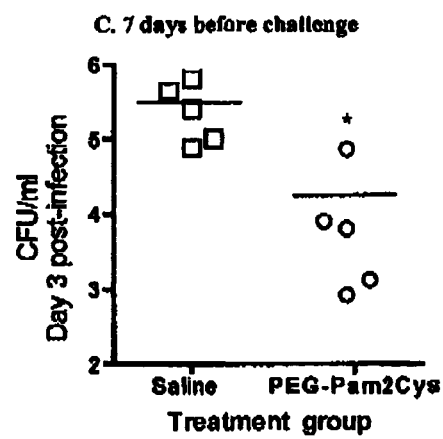

FIG. 16 shows that PEG-Pam2Cys is effective as an anti-bacterial agent. C57BL/6 mice were pre-treated (i.n) with 20 nmol of PEG-Pam2Cys and 3 days later challenged with $1\times10^6$ CFU of *L. pneumophila* (JR32 Δfla strain). Mice were monitored daily after intranasal challenge with *L. pneumophila* and the bacterial load in the lungs of mice was assessed 1, 2 and 3 days after challenge (A). Each symbol represents the mean bacterial load obtained at each time point and the error bars depict the standard deviation (SD). Statistical significance is denoted by (p<0.05) which was obtained using a student's t-test comparing saline and PEG-Pam2Cys treatment groups. The mean percentage bacterial reduction in relation to the saline group is shown above each symbol. To demonstrate the window of PEG-Pam2Cys protection, mice were pre-treated with PEG-Pam2Cys 3 days (B) or 7 days (C) prior to challenge with *L. pneumophila*. Bacterial load at day 3 post-infection is shown in Figures B and C.

DETAILED DESCRIPTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

All publications mentioned in this specification are herein incorporated by reference in their entirety.

It must be noted that, as used in the subject specification, the singular forms "a", "an" and "the" include plural aspects unless the context clearly dictates otherwise. Thus, for example, reference to "an agent" includes a single agent, as well as two or more agents; reference to "the composition" includes a single composition, as well as two or more compositions; and so forth.

In this specification the term "TLR2" is intended to mean Toll-Like Receptor 2 protein. TLR2 is a membrane receptor protein family of Toll-Like Receptors (i.e. "TLRs") including TLR1, TLR3, TLR4, TLR5, TLR6, TLR7, TLR8 and TLR9. In humans. TLR2 is encoded by the TLR2 gene. TLR2 is expressed on the surface of certain cells and plays a fundamental role in pathogen recognition and activation of innate immunity.

A TLR2 agonist is an agent that binds Toll-like receptor 2. The TLR2 agonist may bind TLR2 as a homodimer or heterodimer.

The present invention is predicated on the observation that a TLR2 agonist such as S-[2,3-bis(palmitoyloxy)propyl] cysteine (Pam2Cys) demonstrates the ability to raise an innate immune response in a subject and, in particular, elicit a prophylactic and therapeutic effect against an infectious agent such as a virus (e.g., Influenza A) and bacteria (e.g., *L. pneumophila*) in a non-antigen specific manner.

Thus, in a first aspect of the present invention, there is provided a method for treating or preventing a disease by raising an innate immune response in a subject, the method comprising administering to the subject an effective amount of a composition comprising a TLR2 moiety in solution, wherein the TLR2 moiety comprises a TLR2 agonist and wherein the disease is not treated or prevented by a humoral or cellular immune response directed against the TLR2 moiety.

In some embodiments, the TLR2 agonist is a lipopeptide or comprises a lipid moiety.

An exemplary lipopeptide in accordance with this embodiment of the present invention is the lipopeptide "Pam$_2$Cys". One of skill in the art would understand that the term "lipopeptide" means any composition of matter comprising one or more lipid moieties and one or more amino acid sequences that are conjugated. "Pam$_2$Cys" (also known as dipalmitoyl-S-glyceryl-cysteine or S-[2,3 bis(palmitoyloxy) propyl]cysteine has been synthesised and corresponds to the lipid moiety of MALP-2, a macrophage-activating lipopeptide isolated from *Mycoplasma fermentans*. Pam$_2$Cys is known to be a ligand of TLR2.

Pam2Cys has the structure;

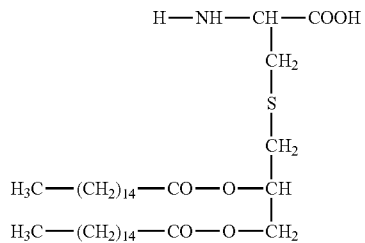

Another exemplary lipopeptide is the lipoamino acid N-palmitoyl-S-[2,3-bis(palmitoyloxy)propyl]cysteine, also known as Pam3Cys or Pam3Cys-OH is a synthetic version of the N-terminal moiety of Braun's lipoprotein that spans the inner and outer membranes of Gram negative bacteria. Pam3Cys has the following structure:

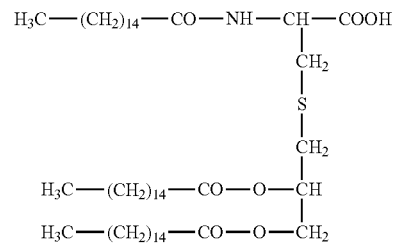

U.S. Pat. No. 5,700,910 describes several N-acyl-S-(2-hydroxyalkyl)cysteines for use as intermediates in the preparation of lipopeptides that are used as synthetic adjuvants, B lymphocyte stimulants, macrophage stimulants, or synthetic vaccines. U.S. Pat. No. 5,700,910 also teaches the use of such compounds as intermediates in the synthesis of Pam3Cys-OH and of lipopeptides that comprise this lipoamino acid or an analog thereof at the N-terminus.

Other lipid moieties which may be used to target cell surface TLRs include palmitoyl, myristoyl, stearoyl, lauroyl, octanoyl, or decanoyl.

In addition to Pam2Cys and Pam3Cys, the present invention also contemplates the use of Set2Cys, Lau2Cys and Oct2Cys according to the present invention. Those skilled in the art will be aware that Set2Cys is also known as S-(2,3-bis(stearoyloxy)propyl)cysteine or distearoyl-5-glyceryl-cysteine; that Lau2Cys is also known as S-[2,3-bis(lauroyloxy)propyl]cysteine or dilauroyl-S-glyceryl-cysteine); and that Oct2Cys is also known as S-[2,3-bis(octanoyloxy) propyl]cysteine or dioctanoyl-S-glyceryl-cysteine).

Other suitable TLR2 agonists include, but are not limited to, synthetic triacylated and diacylated lipopeptides, FSL-I (a synthetic lipoprotein derived from *Mycoplasma salivarium I*), Pam$_3$Cys (tripaltnitoyl-S-glyceryl cysteine) and S-[2,3-bis(palmitoyloxy)-(2RS)-propyl]-N-palmitoyl-(R)-cysteine, where "Pam$_3$" is "tripalmitoyl-S-glyceryl". Derivatives of Pam$_3$Cys are also suitable TLR2 agonists, where derivatives include, but are not limited to, S-[2,3-bis (palmitoyloxy)-(2-R,S)-propyl]-N-palmitoyl-(R)-Cys-(S)-Ser-(Lys)$_4$-hydroxytrihydrochloride; Pam$_3$Cys-Ser-Ser-Asn-Ala; PaM$_3$Cys-Ser-(Lys)$_4$; Pam$_3$Cys-Ala-Gly; Pam$_3$Cys-Ser-Gly; Pam$_3$Cys-Ser; PaM$_3$CyS-OMe; Pam$_3$Cys-OH; PamCAG, palmitoyl-Cys((RS)-2,3-di(palmitoyloxy)-propyl)-Ala-Gly-OH; and the like. Another non-limiting examples of suitable TLR2 agonists are Pam$_2$CSK$_4$ PaM₂CSK₄ (dipalmitoyl-S-glyceryl cysteine-serine-(lysine)₄; or Pam₂Cys-Ser-(Lys)₄) is a synthetic diacylated lipopeptide. Other synthetic TLRs agonists include those described, e.g., in Kellner et al. (1992, *Biol. Chem.* 373:1: 51-5); Seifer et al. (1990, *Biochem. J*, 26:795-802) and Lee et al. (2003, *J. Lipid Res.*, 44:479-486).

As will be understood by persons skilled in the art, TLR2 agonists are typically non-polar and, accordingly, while being soluble in non-polar solvents, are only sparingly soluble in polar and aqueous solvents. Where it is desired to use the TLR2 agonist in a polar or aqueous solvent, the TLR2 agonist may be conjugated with a solubilising agent.

A solubilising agent may include one, or more than one, solubilising agent which may be conjugated to TLR2 agonist in order to improve the solubility of the TLR2 moiety. The solubilising agent will generally be a polar moiety which increases the solubility of the TLR2 moiety in polar or aqueous solvents.

In yet a further embodiment of the present invention, the solubilising agent includes one or more of the group consisting of "PEG" (or polyethyleneglycol) and a polar polypeptide such as "R4", a hyper-branched tetra arginine complex; "H4", a hyper-branched tetra histidine complex; "H8", a linear peptide containing histidine residues; and "E8" a linear peptide containing glutamate residues. Other linear and branched lipid solubilising agents are also envisaged, including a hyper-branched peptide containing glutamate residues (see, e.g., "branched E8", below). In yet a further embodiment of the present invention, the solubilising agent includes PEG and one or more of the group consisting of R4, H4, H8 and E8 (linear or branched). R4, H4, H8 and E8 have been previously described in PCT/AU2009/000469 (WO/2010/115230) and have the following structures:

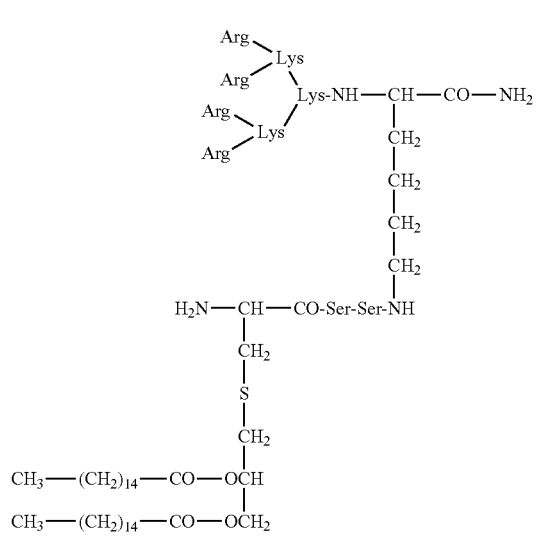
"R4"

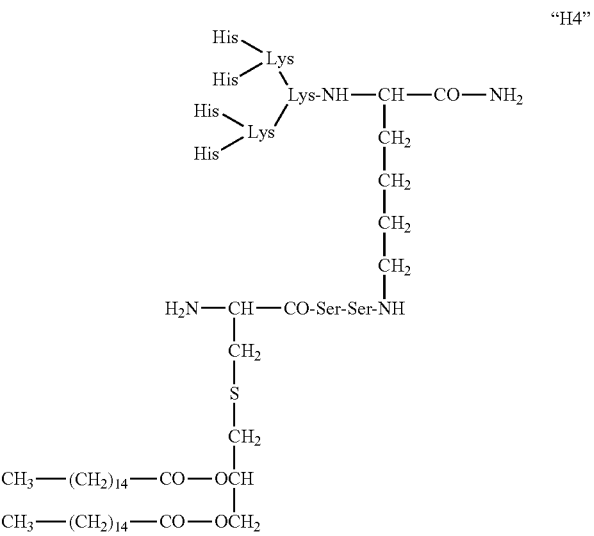
"H4"

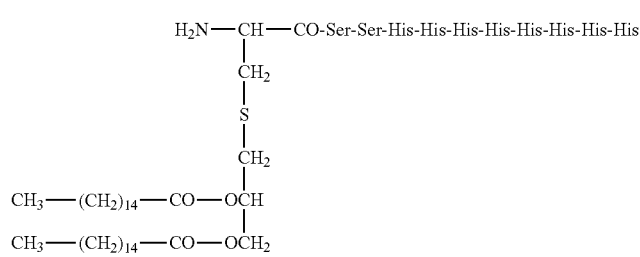
"H8"

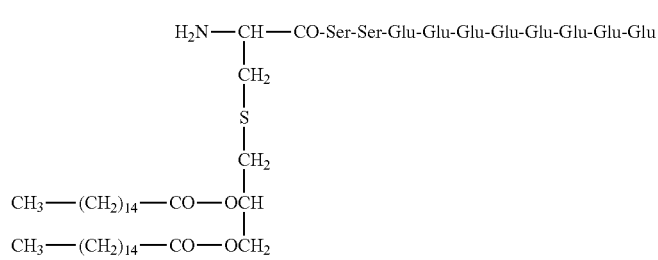
"E8"

-continued

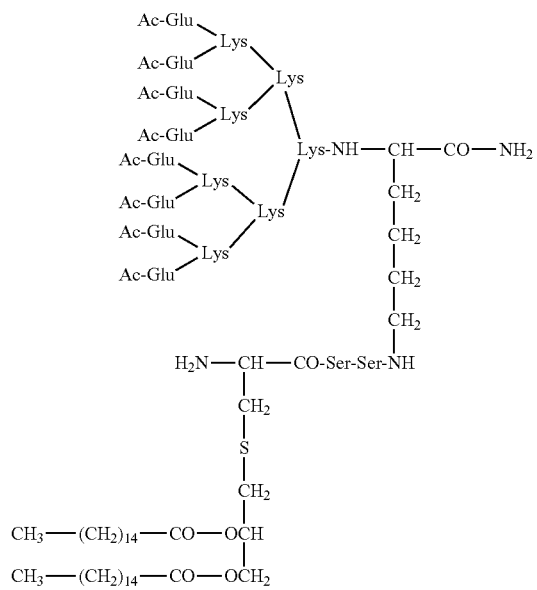

"branched E8"

A person skilled in the art will appreciate that the present invention is not limited to the particular solubilising agents exemplified, and that other suitable solubilising agents known in the art may be used in accordance with the present invention, such as carbohydrates.

The way in which the one or more solubilising agents may be conjugated to a lipid according to the present invention would be well known to a person skilled in the art. For example, conjugation via Fmoc chemistry, through a disulfide or a dioether bridge, or via oxime chemistry is envisaged. In a particular embodiment of the present invention, a soluble form of Pam2Cys was prepared by addition of O—(N-Fmoc-2-aminoethyl)-O'-(2-carboxyethyl)-undecaethyleneglycol (Fmoc-PEG$_{11}$-OH, Merck Ltd) to Pam2Cys. This resulted in the formation of a pegylated form of the lipid, Pam2Cys-PEG$_{11}$ which is then suitable for administration to a subject.

In a particularly preferred form according to the present invention, the TLR2 moiety comprises a conjugate comprising Pam2Cys conjugated to PEG.

As previously indicated, the present inventors have made the surprising observation that Pam2Cys demonstrates prophylactic and therapeutic activity against infection by an infectious agent such as a virus (e.g., Influenza A) or bacteria (e.g., *L. pneumophila*) in a non-antigen specific manner. For instance, when delivered intranasally, a single dose of soluble Pam2Cys provided immediate and significant protection against heterologous subtypes of influenza A infection in C57BL/6, BALB/c and HHD mice as demonstrated by up to 99% reduction in viral loads following mild H3N1 infection, and significantly reduced the morbidity and mortality associated with highly pathogenic H1N1 infection.

The inventors have also found that administering a TLR2 agonist in accordance with the methods of the present invention elicits an innate immune response in a subject in the absence of any co-administered TLR agonist, including a TLR9 agonist. Thus, in some embodiments, the composition according to the present invention does not comprise a TLR9 agonist.

The inventors have shown that the TLR2 agonist according to the present invention can raise a non-antigen specific, innate immune response in a subject. This has been demonstrated by experiments involving administration of a TLR2 moiety comprising one or more peptide antigens, wherein the peptide antigen is "irrelevant" to the disease to be treated or prevented. The term "irrelevant" as used herein is intended to mean not capable of raising a humoral or cellular response to a specific antigen or antigens and, in the context of the present invention, does not raise a humoral or cellular immune response directed against the TLR2 moiety.

Accordingly, the TLR2 agonist according to the present invention may further comprise one or more irrelevant peptide antigens for treatment or prevention of a disease including, but not limited to, T-helper epitopes and/or cytotoxic T-lymphocyte (CTL) epitopes. It is important to bear in mind that since the TLR2 moiety according to the present invention can generate an innate immune response in the subject in a non-antigen specific manner, the skilled person would appreciate that the TLR2 moiety can comprise one or more peptide antigens that will be irrelevant to the disease to be prevented or treated or the TLR2 moiety can be used in the absence of one or more peptide antigens.

By way of illustration, the present invention demonstrates that in the treatment of IAV, a TLR2 moiety comprising one or more "irrelevant" peptide antigens demonstrated the same ability to raise a non-antigen specific/innate immune response following administration of the moiety as the identical TLR2 agonist but without the peptide antigen attached thereto. In these experiments, the inventors used a composition comprising a TLR2 moiety, wherein the TLR2 moiety comprised a TLR2 agonist (e.g., Pam2Cys), a T-helper epitope (OT2) and/or the cytotoxic T lymphocyte epitope Herpes Simplex virus 1-derived CD8+ T cell epitope (refer to Table 1). Both epitopes are irrelevant to IAV. The inventors have thus shown that the TLR2 moiety according to the present invention can raise a non-antigen-dependent, innate immune response in a subject to which it is administered.

Thus, in another aspect of the present invention, there is provided a method for treating or preventing a disease caused by an infectious agent, the method comprising administering to a subject in need thereof an effective amount of a composition comprising a TLR2 moiety in solution, wherein the TLR2 moiety comprises a TLR2 agonist and wherein the TLR2 moiety does not induce a specific cellular or humoral immune response directed against the infectious agent.

In some embodiments, the present invention provides a method for raising an innate immune response in a subject which has an immediate anti-viral effect against a virus following infection. In particular, this means that administration of the TLR2 moiety according to the present invention may have a prophylactic effect following viral infection, and in particular influenza A infection, in the subject. Accordingly, in a further embodiment according to the present invention, administration of the TLR2 receptor agonist may be used in the prophylaxis of disease caused by an infectious agent in the subject. In this way, the methods according to the present invention may be used to elicit an innate immune response in the prophylaxis of infection by infectious agents, including, but not limited to, Influenza A virus (IAV), Hepatitis C virus (HCV), *Mycobacterium tuberculosis, L. pneumophila* and infectious agents known to cause cancer.

The present invention also contemplates a method for raising an innate immune response in a subject that has already been infected or colonised by an infectious agent. In particular, this means that administration of the composition according to the present invention may have a therapeutic effect following infection or colonisation by an infectious agent in the subject. Accordingly, in a further embodiment, administration of the composition according to the present invention may be used in the treatment of disease caused by an infectious agent in the subject.

The inventors have also shown that pre-treated a subject with a TLR2 moiety according to the present invention can significantly reduced bacterial loads in the lung and trachea following intranasal challenge with bacteria, even where infection by bacteria occurs 7 days after administration of the TLR2 moiety. Thus, in some embodiments, the infectious agent is a bacterium. The bacterium can be an intracellular, a gram positive, or a gram negative bacterium. In one embodiment, the bacterium includes, but is not limited to *Staphylococcus, Bacillus, Francisella, Yersinia, Legionella pneumophila* and *Mycobacterium tuberculosis*. In one embodiment, the infectious agent is *Mycobacterium tuberculosis*. In another embodiment, the infectious agent is *Legionella pneumophila*.

In some embodiments, the infectious agent is the cause of a secondary infection in the subject (e.g., pneumonia). Thus, the present invention also provides a method for treating or preventing a secondary infection in a subject by raising an innate immune response, the method comprising administering to the subject an effective amount of a composition comprising a TLR2 moiety in solution, wherein the secondary infection is not treated or prevented by a humoral or cellular immune response directed against the soluble TLR2 moiety.

The present inventors have also demonstrated that, when administered prophylactically, a composition comprising a TLR2 moiety according to the present invention is able to provide immediate protection against mild and pathogenic infection by an infectious agent such as Influenza A and that this protection is associated with the an influx of innate immune mediators into the lung. This anti-viral activity is not antigen-specific.

The present invention also contemplates the use of a TLR2 moiety as defined herein for treating cancer in a subject. Accordingly, in another aspect of the present invention there is provided a method for treating or preventing cancer by raising an innate immune response in a subject, the method comprising administering to the subject a therapeutically effective amount of a composition comprising a TLR2 moiety in solution, wherein the TLR2 moiety comprises a TLR2 agonist and wherein TLR2 moiety does not directly induce a specific cellular or humoral immune response directed against the cancer. In some embodiments, administration of the TLR2 moiety inhibits the growth or spread of cancer.

The skilled person would recognise that the cancer may or may not be caused by an infectious agent. Accordingly, established cancers not caused by infectious agents may also be treated in accordance with the methods of the present invention. For example, the TLR2 moiety may be administered directly to the site of a tumour causing cancer in a subject, so as to induce an innate immune response in the subject. Direct administration of the TLR2 agonist to the site of tumour causing cancer may involve recruitment of cells of the innate immune system (e.g. neutrophils, macrophages and cytokines) to the site of the tumour. Thus, in some embodiments, the composition is administered directly to the site of the tumour causing cancer. The term "tumour" is intended to mean a neoplasm or a solid lesion formed by an abnormal growth of cells (sometimes termed "neoplastic"). It is important to bear in mind that the term tumour is not necessarily synonymous with cancer. A tumour can be benign, pre-malignant or malignant, whereas cancer is by definition malignant, however, in many cases a tumour is associated with cancer. As used herein the term "cancer" refers to a group of diseases and disorders that are characterized by uncontrolled cellular growth (e.g. formation of tumour) without any differentiation of those cells into specialized and different cells.

The term "subject" as used herein refers to an animal, in particular a mammal and more particularly a primate including a lower primate and even more particularly, a human who can benefit from the medical protocol of the present invention. A subject regardless of whether a human or non-human animal or embryo may be referred to as an individual, subject, animal, patient, host or recipient. The present invention has both human and veterinary applications. For convenience, an "animal" specifically includes livestock animals such as cattle, horses, sheep, pigs, camelids, goats and donkeys. With respect to horses, these include horses used in the racing industry as well as those used recreationally or in the livestock industry. Examples of laboratory test animals include mice, rats, rabbits, guinea pigs and hamsters. Rabbits and rodent animals, such as rats and mice, provide a convenient test system or animal model as do primates and lower primates. In some embodiments, the subject is human.

The composition according to the present invention is to be administered in an effective amount. The terms "effective amount" and "therapeutically effective amount" of a TLR2 moiety, as used herein, mean a sufficient amount to provide in the course the desired therapeutic or physiological effect in at least a statistically significant number of subjects. Undesirable effects, e.g. side effects, are sometimes manifested along with the desired therapeutic effect; hence, a practitioner balances the potential benefits against the potential risks in determining what is an appropriate "effective amount". The exact amount required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using only routine experimentation. In some embodiments, an effective amount for a human subject lies in the range of about 0.1 nmol/kg body weight/dose to 1 mol/kg body weight/dose. In some embodiments, the range is about 1 nmol to 1 mol, about 1 µmol to 1 mol, 1 µmol to 500 µmol, 1 µmol to 250 µmol, 1 µmol to 50 µmol, or 1 nmol to 1 µmol/kg body weight/dose. In some embodiments, the range is about 0.08 µmol to 0.11 µmmol/kg body weight/dose of the TLR2 moiety. Dosage regimes are adjusted to suit the exigencies of the situation and may be adjusted to produce the optimum therapeutic dose. For example, several doses may be provided daily, weekly, monthly or other appropriate time intervals.

The terms "treatment" or "treating" include, but are not limited to, (i) slowing or arresting the progression of disease, (ii) partially reversing the progression of disease and (iii) completely reversing the progression of disease (i.e., curing the disease). The terms "prevent" or "preventing" should not be construed as being limited to the complete prevention of disease (i.e., causing the disease not to develop), but may include minimizing the progression of disease, for example, where the disease occurs with less intensity or progresses at a slower rate in a subject as a result of the prophylactic administration of the composition according to the present invention.

The composition according to the invention may be administered in a single dose or a series of doses. While it is possible for the conjugate to be administered alone, it is preferable to present it as a composition, preferably as a pharmaceutically composition. The formulation of such compositions is well known to those skilled in the art. The composition may contain any pharmaceutically acceptable carriers, diluents or excipients. Suitable dosage amounts and dosing regimens can be determined by the attending physician and may depend on the particular condition being treated, the severity of the condition as well as the general age, health and weight of the subject.

By "pharmaceutically acceptable" carrier, excipient or diluent is meant a pharmaceutical vehicle comprised of a material that is not biologically or otherwise undesirable, i.e. the material may be administered to a subject along with the selected conjugate without causing any or a substantial adverse reaction. Carriers may include excipients and other additives such as diluents, detergents, colouring agents, wetting or emulsifying agents, pH buffering agents, preservatives, and the like. Carriers may also include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

Accordingly, the present invention also provides a pharmaceutical composition comprising an effective amount of a TLR2 moiety in solution together with a pharmaceutically acceptable carrier or excipient for treating or preventing a disease by raising an innate immune response in a subject, wherein the TLR2 moiety comprises a TLR2 agonist and wherein the disease is not treated or prevented by a humoral or cellular immune response directed against the TLR2 moiety.

The compositions of the present invention may be administered by any means known to those skilled in the art, including, but not limited to, intranasally, orally and intravenously. In some embodiments, the compositions are administered intranasally.

The present invention also contemplates the use of an effective amount of a TLR2 moiety in solution for the manufacture of a medicament for treating or preventing a disease in a subject, wherein the TLR2 moiety comprises a TLR2 agonist, wherein the TLR2 agonist raises an innate immune response in the subject and wherein the disease is not treated or prevented by a humoral or cellular immune response directed against the TLR2 moiety. Those skilled in the art will appreciate that the invention described herein in susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Certain embodiments of the invention will now be described with reference to the following examples which are intended for the purpose of illustration only and are not intended to limit the scope of the generality hereinbefore described.

Examples

Materials and Methods

Peptide and lipopeptide synthesis, purification and authentication. Lipopeptide and peptide synthesis was carried out by conventional solid phase synthesis using Fmoc (9-fluorenylmethoxy carbonyl) chemistry throughout. Peptides were assembled automatically using a Symphony Multiplex synthesiser (Protein Technologies Inc, Arizona, USA) or a Liberty synthesiser (CEM, North Carolina, USA) which uses microwave technology to facilitate production of high fidelity peptide sequences. Peptides and lipopeptides were purified by reversed phase high performance liquid chromatography and the authenticity of products was determined by mass spectrometry. The procedures used for peptide assembly, purification and characterization have been described in detail elsewhere (1, 2, 3). A soluble form of Pam2Cys was prepared by addition of O—(N-Fmoc-2-aminoethyl)-O'-(2-carboxyethyl)-undecaethyleneglycol (Fmoc-$PEG_{11}$-OH, Merck Ltd) to Pam2Cys. This resulted in the formation of a pegylated form of the lipid, Pam2Cys-$PEG_{11}$. The epitopes included in the lipopeptide constructs and the individual lipopeptide compositions are shown in Table 1.

Animals. 6-8 week old C57BL/6, BALB/c, B6.IFN-γ-/-, B6.IFNAR-/- and HHD nude and female mice were used. HHD "knock out" mice express a chimeric monochain of the α1-α2 domains of HLA-A2.1 and α3 and cytoplasmic and transmembrane domains of $H-2D^b$. These mice are constructed on a double knock out $H-2D^b$-/-β2m-/- mouse, that fails to express serologically detectable murine $H-2D^b$ molecules (4, 5). HHD mice were developed at the Institut Pasteur, Paris, and were kindly supplied by the Queensland Institute for Medical Research. Mice were bred and maintained in the Animal House Facility, Department of Microbiology. B6.IFN-γ$^{-/-}$ mice are deficient in interferon-γ and B6.IFNAR$^{-/-}$ mice do not possess the type 1 interferon receptor. TLR2-deficient mice were kindly provided by Dr Shizuo Akira, Osaka University. All procedures involving mice were approved by The University of Melbourne Animal Experimentation Ethics Committee.

Inoculation procedure. Mice were anaesthetized by Penthrane™ or Isoflurane inhalation and inoculated with 25 mmol of lipopeptide, 25 nmol of the non-lipidated peptide or 2-20 nmol Pam2Cys containing constructs by the intranasal route. Pam2Cys containing constructs and lipopeptides and peptide were dissolved in saline and administered in a volume of 50 µl while saline control groups received 50 µl of saline only.

Challenge with influenza a virus. On day 1, 3 or 7 following inoculation with lipopeptide mice were challenged intranasally with live IAV. For mild IAV infection, mice were administered $10^{4.5}$ PFU of the H3N1 virus, Mem71, a genetic reassortant of A/Memphis/1/71 [H3N2]× A/Bellamy/42 [H1N1]. On day 5 of challenge, lungs were harvested for determination of viral titres and spleens harvested for characterization of the CD8$^+$ T cell responses. Challenge with highly pathogenic IAV was carried out using 50 PFU (HHD mice), 200 PFU (C57BL/6 mice) or 500 PFU (BALB/c mice) of the H1N1 virus A/Puerto Rico/8/34 (PR8) via the intranasal route. This highly pathogenic virus induces a symptomatic infection characterised by weight loss and dehydration. Mice were monitored daily for signs of morbidity and culled when necessary at a humane end point which was determined using a combination of clinical symptoms and degree of weight loss approved by The University of Melbourne Animal Ethics Committee.

Challenge with *Legionella pneumophila* bacteria. C57BL/6 mice were intranasally pre-treated with 20 nmol of PEG-Pam2Cys 3 days prior to intranasal challenge with $1 \times 10^6$ CFU of *L. pneumophila* (JR32 Δfla strain). The bacterial load in the lungs of mice was assessed 1, 2 and 3 days after infection.

Contact Transmission Study. To assess viral transmission in BALB/c mice, "donor" mice (n=2) received $10^{4.5}$ pfu of the H3N2 Udorn virus (A/Udorn/72) in 50 µl of saline by the intranasal route. One day following challenge, donor mice were co-housed with naive "recipient" mice (n=3) for 24 hrs after which the donor mice were removed and nasal turbinates, trachea and lungs harvested and assessed for viral titres. Three and a half days following exposure to donor mice, the nasal turbinates, trachea and lungs of recipient mice were harvested for assessment of viral titres. This protocol is based on a contact transmission model developed by Edenborough et al (in preparation).

Assessment of viral titres in nasal turbinates, trachea and lungs. The nasal turbinates, trachea and lungs of mice were homogenized in 3 ml of RPMI and the titers of IAV virus in the lung supernatants were determined using a Medine Darby Canine Kidney (MDCK) Plaque Assay as described previously (6).

Preparation of single-cell suspensions from organs. Following $CO_2$ asphyxiation, the lungs of mice were perfused with 10 ml of PBS via the right ventricle of the heart to remove circulating cells. Lungs were cut into pieces and subjected to enzymatic digestion with collagenase A (2 mg/ml, Roche, Mannheim, Germany) in RPMI for 30 mins. Digested lung fragments were strained through a sieve and treated with 3 ml pre-warmed Tris-buffered ammonium chloride solution (ATC) for 2 minutes at room temperature in order to lyse erythrocytes. Lung cells were then washed twice in RP10 (RPMI 1640 medium [Gibco, USA] supplemented with 10% FCS [CSL, Parkville, Australia] 7.5 mM HEPES, 2 mM L-glutamine, 76 µM 2-mercaptoethanol, 150 U/ml penicillin, 150 µg/ml streptomycin and 150 µM non-essential amino acids [Gibco]. Spleens were collected into 10 ml of RP10 and single cell suspensions prepared by disruption through a sieve and then treated with ATC for 5 minutes at 37° C. Cells were washed twice with RP10 before use. To obtain Bronchoalveolar lavage (BAL) Fluid the mouse tracheas were cannulated with a syringe and the air space was flushed with three separate 1 ml washes of RPMI, and a final 1 ml rinse of the syringe. The supernatant from the BAL washes was stored at −70° C. for later cytokine analysis. The supernatant from the BAL washes was stored at −70° C. for later cytokine analysis. Viable cells counted using a haemocytometer and trypan blue dye exclusion.

Characterisation of the pulmonary cytokine environment. Cytokine levels in the BAL supernatant was determined using a BD™ Cytometric bead array (CBA) (Biosciences) Mouse Inflammation Kit according to the manufactures instructions, with the exception that only 2 µl of each capture bead was used for each 50 µl BAL sample. Standard curves (20-5000 pg/ml) were prepared for the following cytokines interleukin-6 (IL-6), interleukin-10 (IL-10), monocyte chemoattractant protein-1 (MCP-1), Interferon-γ (IFN-γ), tumor necrosis factor-α (TNF-α) and interleukin-12p70 (IL-12p70). Cytokine concentrations were determined from neat, or 1/10 dilutions of the BAL supernatant. Samples were analysed using a Becton Dickinson FACSCalibur flow cytometer and FlowJo software.

Characterisation of lung cells. $5 \times 10^5$ lung cells were stained with combinations of the following anti-mouse antibodies; FITC labelled anti-CD11b, PerCP-Cy5.5 Anti-GR-1 (Ly-6G and Ly-6GC), PE-labelled anti-CD11c, APC anti-F4/80, FITC anti-IA/IE class 2, PerCP-Cy5.5 anti-CD8, PE anti CD4 (BD Pharminigen). Pulmonary cell subsets were classified as follows; Neutrophils: CD11b$^{hi}$, GR1$^{hi}$, CD11c$^-$, F4/80$^-$; alveolar macrophages: CD11c$^{hi}$, F4/80$^+$, CD11b$^{int/lo}$, GR1$^{int/lo}$ and CD11c$^{hi}$, Autofluorescence$^{hi}$; dendritic cells: CD11c$^{hi}$, and MHC Class 2$^{hi}$, GR1$^{int}$; monocytes and interstitial macrophages: CD11b$^{hi}$, GR1$^{int}$, CD11c$^{int/lo}$), F4/80$^+$; CD8$^+$T cells: CD8$^+$; CD4$^+$T cells: CD4$^+$ (7, 8, 9).

Intracellular cytokine staining (ICS) assay. Single cell suspensions of lung or spleen cells were stimulated with peptide at 1 µs/ml (C57BL/6 and BALB/c) or 10 ug/ml (HHD) for 6 hr at 37° C. in the presence of 5 µg/ml GolgiPulg (BD Biosciences Pharmingen) 25 U/ml and recombinant human IL-2 (Roche, Indianapolis, USA) in a total volume of 200 µl RP10. Cells were stained with PerCP (Cy5.5) labelled with rat anti-mouse CD8α antibody (BD Biosciences Pharmingen) for 30 min on ice. Cells were fixed and permeabilised using the BD Cytofix/Cytoperm kit TM (BD) according to the manufacturers directions and stained with FITC-labelled anti-IFN-γ and APC-labelled anti-TNF-α (BD Biosciences Pharmingen) for 30 min at 4° C. Samples were analysed using a Becton Dickinson FACSCalibur flow cytometer and analysed using FlowJo software.

Statistical analyses. For time point comparisons, a one-way ANOVA (post-hoc Dunnett's multiple comparison test) was used to determine differences between the pre-inoculation (Day 0) group to the post-inoculation (Day 1, 3, 6, 8) groups. For other studies, a two-tailed unpaired student's t-test or one-way ANOVA (post-hoc Tukey's multiple comparison test) were used to determine statistical differences between two or more than two groups respectively. A P value of <0.05 was considered significant.

Results

Figure 1:
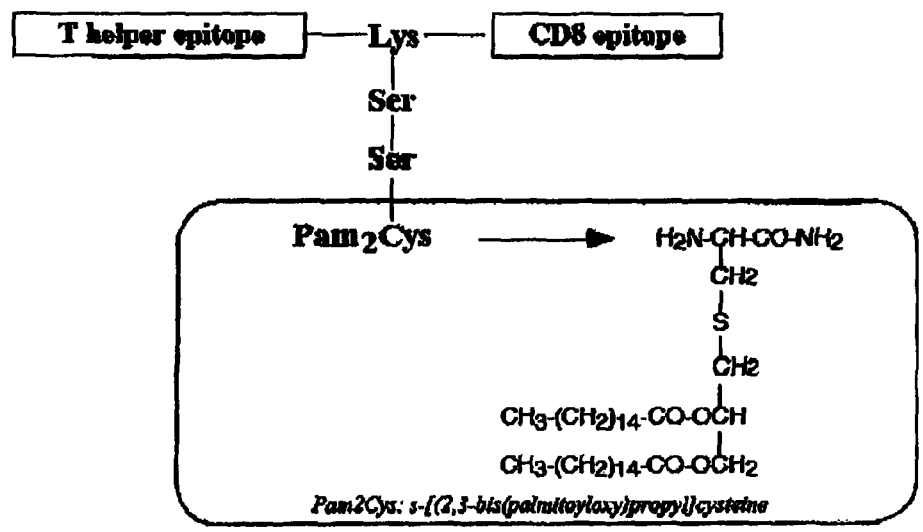
FIG. 1 shows a schematic representation of lipopeptide vaccine candidates. Schematic representation of Pam2Cys-based constructs. (A) Pegylated Pam2Cys (Pam2Cys-PEG$_{11}$) consists of a single Pam2Cys molecule coupled to undecaethyleneglycol (polyethelene glycol, PEG) via two scenes. (B) Pam2Cys-based lipopeptide vaccine candidates are composed of a target CD8$^+$ T cell epitope and T helper epitope linked through a single lysine (K) residue. The Pam2Cys lipid moiety is attached via two serine residues (Ser) to form a branched peptide structure.
Figure 1:
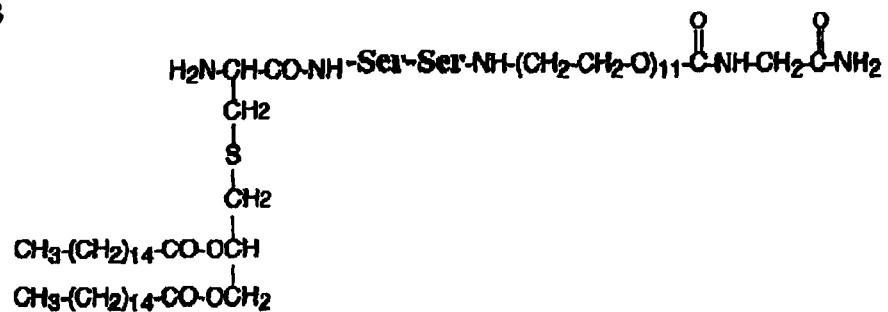
Figure 2:
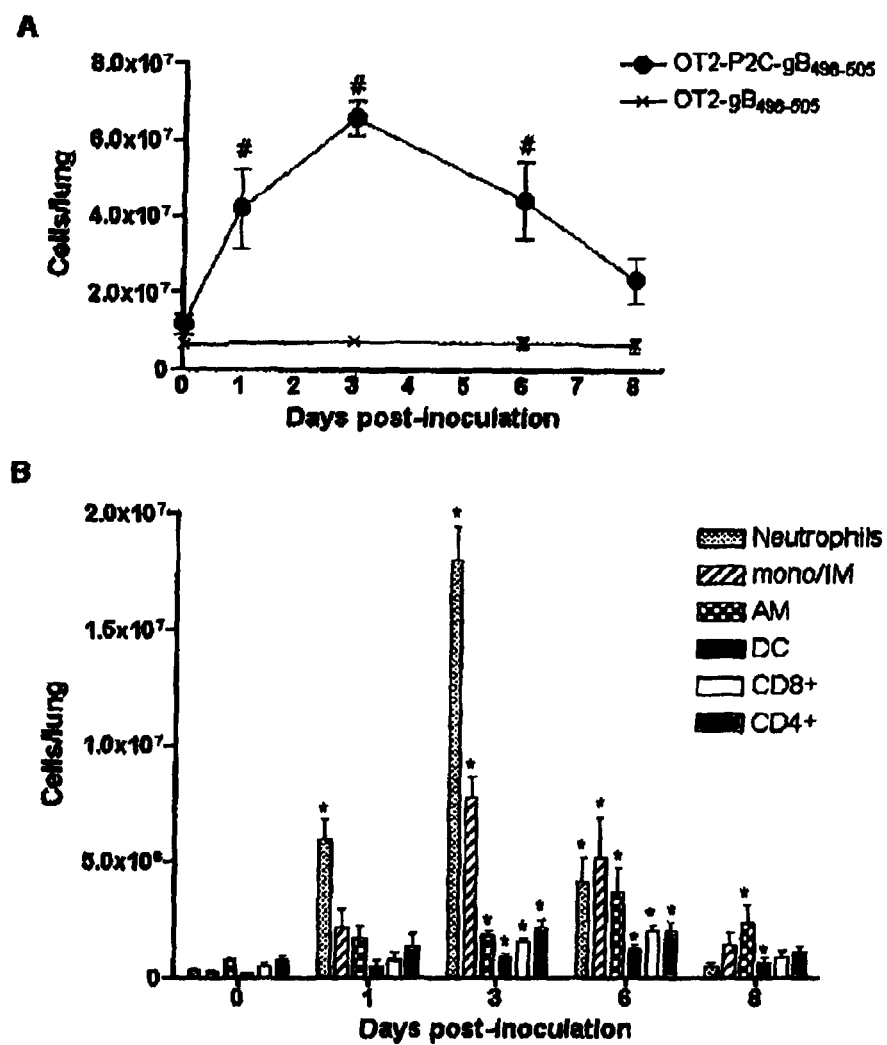
FIG. 2 shows intranasal administration of lipopeptide expands pulmonary cell populations. C57BL/6 mice were inoculated intranasally with 25 nmol of the OT2-P2C-gB$_{498-505}$ lipopeptide or 25 nmol of the peptide OT2-gB$_{498-505}$ (lacking Pam2Cys) and characterisation of the lung cell populations was performed at the indicated time points (n=3/group/time point). (A) The total number of lung cells is shown. Symbols represent the mean cell count and the error bars indicate the SEM, #=P<0.01 vs. day 0. (B) The composition of lung cells is shown. Each bar represents the mean cell count (n=3) and the error bars indicate the SD, *=P<0.05 vs the cell population at day 0. Statistical analyses were carried out using one-way ANOVA analysis and post-hoc Dunnett's multiple comparison test. A repeat experiment yielded similar results.

Pam2Cys-based lipopeptide inoculation expands the pulmonary cell populations. The effect of Pam2Cys-based lipopeptide on the pulmonary cellular environment was examined in C57BL/6 mice which were inoculated intranasally with the lipopeptide OT2-P2C-gB$_{498-505}$ containing the T helper epitope (Th) OT2 and a Herpes Simplex virus 1-derived CD8$^+$ T cell epitope (gB$_{498-505}$; see Table 1). The lung resident cell populations in lungs perfused with PBS were characterised using cell flow cytometry. Intranasal inoculation with OT2-P2C-gB$_{498-505}$ elicited a dramatic increase in the total number of lung cells that reached a maximum on day 3 and remained elevated until day 8 (FIG. 2A). In contrast, mice that received the peptide OT2-gB$_{498-505}$ (lacking Pam2Cys) showed no significant changes in the total number of cells or proportion of cell types present in the lungs, pointing towards Pam2Cys as the mediator of the cellular influx (FIG. 2A). In lipopeptide-inoculated mice, the cellular infiltrate at day 3 following inoculation, was largely composed of neutrophils and interstitial macrophages (FIG. 2B). Microscopic examination by Giemsa staining revealed that the neutrophils exhibited an highly vacuolar phenotype; indicating activation, while the F480$^+$ monocyte/interstitial macrophage population was found to be predominantly composed of interstitial macrophages with a large and nucleated morphology with few cells possessing the donut or kidney-shaped nucleus characteristic of monocytes were identified (data not shown). Although alveolar macrophages (AM) were present at very low levels in the steady state lung (day 0), a significant increase in this population was evident following lipopeptide inoculation. Finally, we also observed increases in the CD4$^+$ and CD8$^+$ lymphocytes and CD11c$^{hi}$ dendritic-like cells between day 3-8 post-inoculation. An examination of the pulmonary cell influx of BALB/c and HHD mice revealed similar patterns of early neutrophil infiltration followed by expansion of the interstitial macrophage and CD11b$^{hi}$ alveolar macrophage populations (data not shown).

Pegylated Pam2Cys administration expands pulmonary cell populations. Intranasal administration of pegylated Pam2Cys (P2C-PEG$_{11}$) also resulted in significant increases in the total lung (includes the lung interstitium and HAL fluid-containing) populations of neutrophils, interstitial and alveolar macrophages and lymphocytes in C57BL/6 (FIG. 7) and BALB/c mice (data not shown). Increased levels of activated IFN-γ producing NK cells and γδ T cells were also observed (FIG. 7).

Pam2Cys prophylaxis is effective against highly pathogenic IAV challenge. To determine if the anti-viral activity of Pam2Cys is effective against a virulent strain of IAV, mice that received pegylated Pam2Cys (P2C-PEG$_{11}$) were challenged 72 hr or 7 days later with a lethal dose of the H1N1 virus PR8. The saline-treated (challenged 72 hr later) mice experienced substantial weight loss, developed clinical symptoms of infection and by day 8 all mice had succumbed to the infection (FIG. 8). In contrast the mice pre-treated with PEG-Pam2Cys experienced substantially lower weight loss and all mice survived infection (FIG. 8).

Pam2Cys prophylaxis can reduce transmission rates. To determine if influenza infected mice pre-treated with Pam2Cys have a reduced capacity to transmit virus, a mouse model of contact transmission was utilised (Edenborough et al., in preparation). "Donor" mice that were pre-treated with PEG-Pam2Cys were challenged at various time points thereafter with 10$^{4.5}$ pfu of H3N2 Udorn virus. The results show that Pam2Cys prophylaxis reduces nasal, tracheal and lung viral titres (FIG. 9). All the recipient mice that were co-housed with saline-treated donor mice became infected confirming the ability of the donor mice to transmit virus. Although mice that had received Pam2Cys 5 or 7 days prior to challenge transmitted virus to recipient mice, mice that had received Pam2Cys 24 hrs or 72 hrs prior to virus challenge did not transmit the infection to co-housed recipient mice.

Intranasal delivery of lipopeptide provides immediate protection against IAV challenge. To determine whether the pulmonary changes induced by intranasal delivery of lipopeptide could reduce the impact of IAV challenge, the protective affect of lipopeptide inoculation against a mild (H3N1) and highly virulent PR8 (H1N1) IAV viruses was examined. Three strains of mouse were administered lipopeptide containing an IAV-specific CD8$^+$ T cell epitope (IAV-LP) restricted to the particular mouse strain or an irrelevant non-IAV-derived CD8$^+$ T cell epitope (non-IAV-LP) (Table 1). In all lipopeptides, the CD4$^+$ Th cell epitope was unrelated to influenza virus. (Table 1). While the IAV-LP is capable of inducing CD8$^+$ T cell responses to the delivered IAV-derived epitope the absence of IAV-specific epitopes (CD8$^+$ T or CD4$^+$) in the non-IAV-LP means that IAV-specific responses will not be induced on inoculation.

Figure 3:
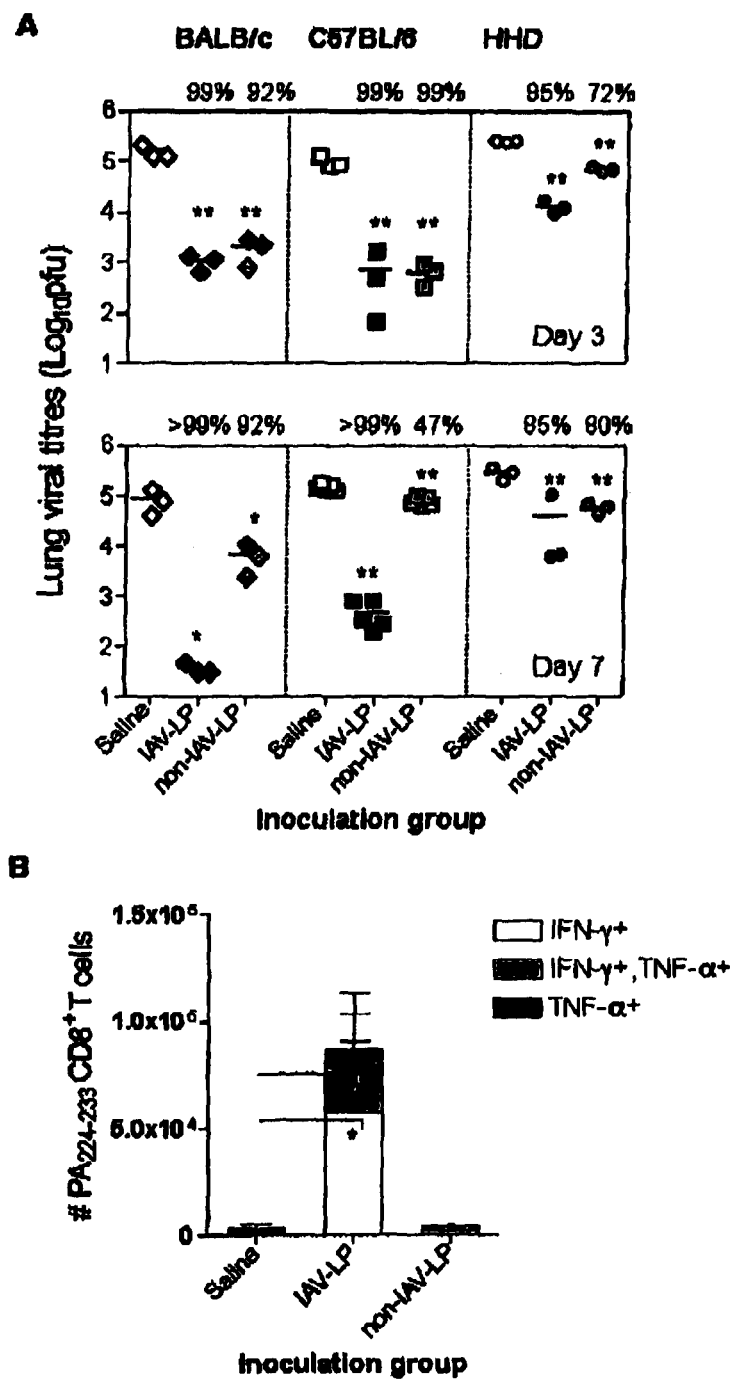
FIG. 3 shows Pam2Cys-based lipopeptides enhance the clearance of IAV. (A) Mice were inoculated with saline, IAV-LP (containing an IAV-derived epitope) or non-IAV-LP and challenged at day 3 (upper panel) or day 7 (lower panel) following lipopeptide inoculation with 10$^{4.5}$ pfu of Mem71 (H3N1) influenza virus (n=3-5/group). Lung viral titres were assessed at day 5 of infection and are shown for BALB/c (◇), C57BL/6 (□) and HHD (○) mice. Symbols represent the titre obtained from an individual mouse and the line indicates the mean virus titre of the group. (B) The percentage of viral clearance relative to the saline control is shown above the lipopeptide groups. IAV-specific CD8$^+$ T cell responses were detected from C57BL/6 mice challenged with Mem71 on day 7 after LP inoculation. On day 5 of challenge PA$_{224-233}$-specific CD8$^+$ T cells were detected from the spleen using an intracellular staining assay for IFN-γ and TNF-α. Bars indicate the mean cytokine-specific response in each group and the error bars indicate the SD. *=P<0.05, **P<0.01 vs Saline (one-way ANOVA analysis and post-hoc Dunnett's multiple comparison test.

C57BL/6, BALB/c and MID mice were challenged intranasally with 10$^{4.5}$ PFU H3N1 virus, Mem71, either 3 or 7 days following inoculation with either IAV-LP or non-IAV-LP and lung viral titres were assessed on day 5 of infection. The results in FIG. 3A show that in all strains of mice, inoculation with the IAV-LP as well as the non-IAV-LP resulted in significant reduction of lung virus titres when compared to animals that did not receive lipopeptide. In the non-IAV LP group, viral clearance was most striking when challenge occurred 3 days after inoculation (FIG. 3A).

The absence of IAV-specific epitopes (CD8$^+$ T or CD4$^+$) in the non-IAV-LP suggested that the anti-viral activity of non-IAV-LPs is conferred by the Pam2Cys moiety. To confirm this theory, we examined the presence of IAV-specific CD8$^+$ T cell responses to PA$_{224-233}$) an immunodominant UV-specific target in C57BL/6 mice, and the same epitope included in the IAV-LP but not in non-IAV-LP, In lipopeptide inoculated C57BL/6 mice, only mice that received IAV-LP showed significant levels of IFN-γ$^+$ or IFN-γ$^+$ TNF-α$^+$ PA$_{224-233}$-specific CD8$^+$ T cells while neither the saline nor the non-IAV-LP groups elicited detectable responses to these epitopes (FIG. 3B). This same pattern of T cell responses was observed in the BALD/c and HHD mouse strains. The absence of IAV-specific cells in mice inoculated with non-IAV-LP demonstrates that the early anti-viral effect observed is due to the action of Pam2Cys and not to an accelerated ability to mount an IAV-specific adaptive immune response.

It should be noted that the non-IAV LP, in contrast to IAV-LP, does not provide long-term protection associated with the induction of IAV-specific CD8$^+$ T cell responses. Only IAV-LP inoculated BALB/c and C57BL/6 mice exhibited significant levels of viral clearance (98±1% and 65±14% (respectively)) if challenged with H3N1 occurs 6-8 weeks following inoculation (data not shown). Therefore, in the absence of antigen specific responses, the anti-viral activity of non-IAV LPs is reduced with time demonstrating that the we T cell epitope component of the lipopeptide is essential to long-term protection with IAV-LPs.

Figure 4:
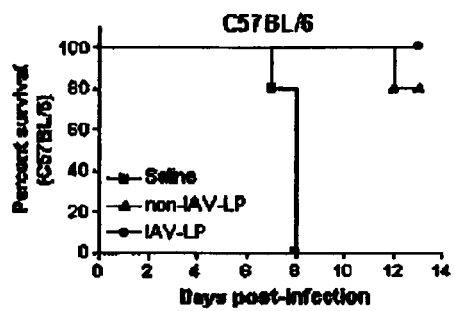
FIG. 4 shows PamCys-based lipopeptides reduce the impact of highly pathogenic IAV infection. Upper panels.
Figure 4:
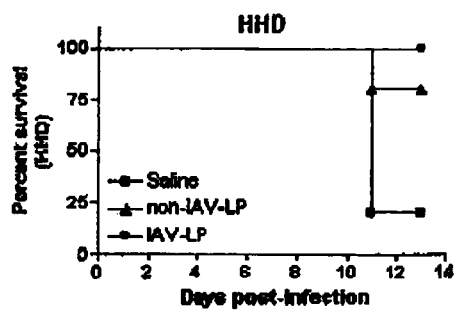
Figure 4:
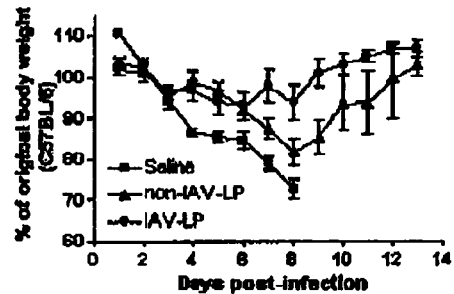
Figure 4:
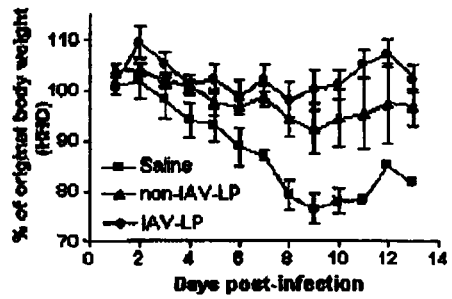

Lipopeptide prophylaxis is effective against highly pathogenic IAV challenge. To determine if the anti-viral activity of Pam2Cys was effective against highly pathogenic infection, lipopeptide inoculated mice were challenged 7 days later with the highly pathogenic H1N1 virus, PR8. Both IAV-LP and non-IAV LP lipopeptide inoculation dramatically increased the survival rate in mice challenged with PR8 (FIG. 4). While the majority of mice inoculated with saline succumbed to infection, 100% of animals inoculated with IAV-LP and 80% of animals inoculated with non-IAV-LP survived the infection. In addition to improved survival rates, the degree of weight loss and clinical symptomology that is normally associated with infection was also reduced in the non-IAV-LP group (FIG. 4).

Pam2Cys protects against IAV when delivered intranasally in a single dose. Following prophylactic administration of pegylated Pam2Cys (PEG-Pam2Cys) (also referred to herein as Pam2Cys-$PEG_{11}$ or P2C-$PEG_{11}$) in mice via the intranasal (i.n), subcutaneous (s.c) or intravenous (i.v) routes and a subsequent challenged with a lethal dose of PR8 virus 3 days later, only the mice administered PEG-Pam2Cys intranasally wore protected against death and weight loss associated with PR8 infection (FIG. 10).

TABLE 1

Details of the mouse strains and lipopeptides used in the present invention

| Mouse strain | MHC class I phenotype | $CD8^+$ T cell target epitope sequence | Origin of $CD8^+$ T cell epitope | MHC Class I restricting element | Components of IAV-LP | Components of non-IAV-LP |
|---|---|---|---|---|---|---|
| C57BL/6 | $H-2K^b$ $H-2D^b$ | SSLENFRAYV(10) | IAV polymerase A ($PA_{224-233}$) | $H2-D^b$ | $OT2^{ii}$-$P2C^{iii}$-$PA_{224-233}$ | |
| | | SSIEFARL(11) | glycoprotein B of HSV-1 ($gB_{492-505}$) | $H2-K^b$ | | OT2-P2C-$gB_{494-505}$ |
| $^i$HHD | HLA-A2.1 | GILGFVFTL(12) | IAV M1 protein ($M1_{58-66}$) | HLA-A2.1 | OT2-P2C-$M1_{58-66}^{iv}$ | OT2-P2C-$gB_{498-505}$ |
| | | FMYSDFHFI(13) | IAV polymerise A ($PA_{46-55}$) | | OT2-P2C-$PA_{46-55}$ | |
| | | AIMDKNIIL(14) | IAV non-structural protein ($NS1_{122-130}$) | | OT2-P2C-$NS1_{122-130}$ | |
| BALB/c | $H-2K^d$ $H-2D^d$ | TYQRTRALV(15, 16) | IAV nucleoprotein ($NP_{147-155}$) | $H2-K^d$ | $P25^v$-P2C-$NP_{147-155}$ | P25-P2C-$PA_{224-233}^{vi}$ |

$^i$HHD mice are a transgenic strain that exclusively express chimeric HLA-A2.1 class I molecules
$^{ii}$OT2 (amino acid sequence ISQAVHAAHAEINEAGR) is a Th epitope from ovalbumin.
$^{iii}$P2C: Pam2Cys
$^{iv}$An admixture of the three IAV-LPs were administered to HHD mice prior to challenge with the H1N1 PR8. Mice challenged with H3N1 Mem71 only received OT2-P2C-$M1_{58-66}$.
$^v$P25 (amino acid sequence KLIPNASLIENCTKAEL) is a promiscuous Th epitope (16) from morbilli viruses.
$^{vi}$The $PA_{224-233}$ epitope is not recognised by the Class 1 restriction molecules present in BALB/c mice.

The spectrum of cytokines induced by soluble Pam2Cys. To remove the influence of peptide, or epitope-specific responses from the system, we constructed a soluble form of Pam2Cys by conjugating the normally insoluble Pam2Cys to polyethylene glycol (PEG). To identify the impact of Pam2Cys-$PEG_{11}$ on the pulmonary environment, we measured the concentration of inflammation-associated cytokines in the Bronchoalveolar lavage (BAL) fluid of C57BL/6 mice administered 20 nmol Pam2Cys-$PEG_{11}$ (i.n) by cytometric bead array analysis (FIG. 5). On day 3 following administration, we detected significant increases in IL-6, IL-10, MCP-1, TNF-α and IL-12p70 concentrations in Pam2Cys-$PEG_{11}$ inoculated mice in comparison to naive or saline inoculated mice. By day 7, the cytokine concentrations in the Pam2Cys-$PEG_{11}$ group had normalised to pre-administration levels and did not differ significantly to the naive group (FIG. 5).

The antiviral activity of Pam2Cys is antigen-independent. To confirm that the Pam2Cys moiety is mainly responsible for the early anti-viral activity of lipopeptides, mice were inoculated intranasally with 20 nmol of Pam2Cys-$PEG_{11}$ and challenged with $10^{4.5}$ PFU H3N1 virus either 1, 3 or 7 days later. The results shown in FIG. 6 demonstrate that inoculation with Pam2Cys-$PEG_{11}$ reduces lung viral loads to the same extent as non-IAV-LP, confirming that the early antiviral activity of lipopeptides observed is mediated by Pam2Cys. Prophylaxis with Pam2Cys-$PEG_{11}$ reduced the viral load following challenge almost immediately, at day 1 and out to day 7 post-administration, revealing that at least a 7 day window of protection can be provided by Pam2Cys-$PEG_{11}$ prophylaxis.

Multiple Pam2Cys variants confer protection against IAV challenge. Mice that were prophylactically administered 20 nmol of various Pam2Cys-containing constructs via the intranasal routes were protected against weight loss (FIG. 11A) and death (FIG. 11B) following a challenge with a lethal dose of PR8 virus. Mice were also protected against other clinical symptoms associated with PR8 infection (data not shown).

Pam2Cys is effective when given in a repeated dose. Balb/c mice administered a single dose of PEG-Pam2Cys (or two doses of PEG-Pam2Cys three weeks apart) were protected against weight loss (FIG. 12B), death and other the clinical symptoms following a challenge with lethal dose of PR8. Viral loads in PEG-Pam2Cys-treated mice were significantly lower at the time of culling (FIG. 12A).

PEG-Pam2Cys is effective at lower doses. When mice were prophylactically treated with lower doses of PEG-Pam2Cys and challenged 3 days later with a lethal dose of PR8 virus, protection against weight loss and death was still achieved in all mice compared to the saline group (FIG. 13).

Protection against IAV challenge is not dependent on IFN-γ or type 1 interferons (i.e. IFN-α). Mice deficient in IFN-γ (B6.IFN-γ-/-) or in the ability to respond to type 1 interferon (such as interferon-α; IFNAR-/-) that were treated with PEG-Pam2Cys were protected against the weight loss and lethality associated with PR8 infection (FIG. 14).

PEG-Pam2Cys is effective as a therapeutic agent. When mice were challenged with $10^{4.5}$ PFU of Udorn virus (Influenza A) (i.n.) and 4 hours later administered 20 nmol PEG-Pam2Cys (i.n.), reduced viral loads were found in the nose, oropharynx, trachea and lung. Viral load in the lungs, in particular, showed a $Log_{10}4$, or 10,000 fold reduction as compared to the Saline group (FIG. 15).

Pam2Cys is effective as an anti-bacterial agent. When mice were pre-treated with PEG-Pam2Cys (i.n.), they showed significantly reduced lung and trachea bacterial loads following i.n. challenge with *L. pneumophila* (FIG. 16A). The bacterial load in the lungs peaked on day 2 and 3. Reduced bacterial loads can also be achieved up to 7 days after PEG-Pam2Cys administration and bacterial loads at day 3 post infection is shown for mice which received PEG-Pam2Cys prophylaxis 3 (FIG. 16B) or 7 days (FIG. 16C) before challenge.

Discussion

The crucial role that the innate immune response plays in control of infection suggests that early activation of the innate immune system prior to infection could provide enhanced protection against a challenge by an infectious agent, such as a virus or bacterium. The results of this study demonstrated that administration of a soluble TLR2 moiety comprising a TLR2 agonist raises an innate immune response in a subject to which it is administered, wherein the immune response is non-antigen specific. Moreover, the pulmonary changes elicited by prophylactic intranasal administration of the composition according to the present invention were associated with an increased resistance to subsequent exposure to virus and bacteria, suggesting that such compositions are suitable as prophylactic agents against viral and bacterial infection, particularly when there is high risk of epidemic or pandemic outbreaks. The prophylactic and therapeutic methods according to the present invention also have the advantage of not requiring prior knowledge of the infectious agent (or its antigenic components or particular strain) and therefore could be particularly useful, for example, during influenza pandemics. The stability of composition according to the present invention, which can be freeze dried and is stable at room temperature, also means it is highly suitable for stockpiling in preparation for a pandemic situation.

REFERENCES

1. Jackson, D. C., et al 2004. *Proc Natl Acad Sci USA* 101:15440-5.
2. Zeng, W., et al. 2005. *Vaccine* 23:4427-35.
3. Zeng, W., et at 2002. *J Immunol* 169:4905-12.
4. Firat, H., et al. 1999. *Eur J Immunol* 29:3112-21.
5. Pascolo, S., et al 1997. *J Exp Med* 185:2043-51.
6. Tannock, G. A., et al. 1984. *Infect Immun* 43:457-62.
7. Cleret, A., et al. 2007. *J Immunol* 178:7994-8001.
8. Gonzalez-Juarrero, M., et al. *J Immunol* 171:3128-35.
9. Landsman, L., and S. Jung. 2007. *J Immunol* 179:3488-94.
10. Belz, G. T., et al. 2000. *J Virol* 74:3486-93.
11. Wallace, M. E., et al. 1999. *J Virol* 73:7619-26.
12. Gotch, F., et al. 1987. *Nature* 326:881-2.
13. Gianfrani, C., et al. 2000. *Hum Immunol* 61:438-52,
14. Jameson, 3., et al. 1999. *J Immunol* 162:7578-83.
15. Bodmer, H. C. et al. 1988. *Cell* 52:253-8.
16. Sherman, L. A., et al. 1992. *J Exp Med* 175:1221-6.

The invention claimed is:

1. A method for preventing or treating a respiratory condition associated with one or more viral infectious agents in a subject, the method comprising:

administering to the respiratory tract of the subject a composition comprising a soluble TLR2 moiety comprising a TLR2 agonist and a solubilizing agent that increases the solubility of the TLR2 agonist in polar or aqueous solvents, thereby preventing or treating the respiratory condition in the subject, wherein the moiety raises an innate immune response in the subject and does not raise an immune response that is specific for an antigen of the one or more infectious agents, wherein the composition does not contain a peptide antigen comprising a T-helper epitope, and wherein the TLR2 agonist is a lipopeptide.

2. The method according to claim 1, wherein the TLR2 agonist is selected from the group consisting of S-[2,3-bis(palmitoyloxy)propyl]cysteine ($Pam_2Cys$), N-palmitoyl-S-[2,3-bis(palmitoyloxy)propyl]cysteine ($Pam_3Cys$), S-[2,3-bis(stearoyloxy)propyl]cysteine, S-[2,3-bis(lauroyloxy)propyl]cysteine, and S-[2,3-bis(octanoyloxy)propyl]cysteine.

3. The method according to claim 2, wherein the TLR2 agonist is $Pam_2Cys$.

4. The method according to claim 1, wherein the soluble TLR2 moiety comprises polyethyleneglycol (PEG) or a polar polypeptide.

5. The method according to claim 4, wherein the polar polypeptide is selected from the group consisting of R4, K4, H4, E8, branched E8and H8.

6. The method according to claim 4, wherein the soluble TLR2 moiety comprises polyethyleneglycol (PEG).

7. The method according to claim 1, wherein the soluble TLR2moiety comprises polyethyleneglycol (PEG) and any one of R4, K4, H4, E8, branched E8 and H8.

8. The method according to claim 1, wherein the soluble TLR2moiety is R4Pam2Cys.

9. The method according to claim 1, wherein the soluble TLR2 moiety is PEG-Pam2Cys.

10. The method according to claim 1, wherein the soluble TLR2 moiety is E8Pam2Cys.

11. The method according to claim 1, wherein the soluble TLR2 moiety is H8Pam2Cys.

12. The method according to claim 1, wherein the composition is administered intranasally to the subject.

13. The method according to claim 1, wherein the virus is Influenza A virus (IAV).

14. The method according to claim 1, wherein a TLR9 agonist is not administered.

15. The method according to claim 1, wherein the soluble TLR2 moiety does not comprise a peptide antigen.

16. The method according to claim 1, wherein the soluble TLR2 moiety does not comprise an antigen.

17. The method according to claim 1, wherein the soluble TLR2 moiety consists of a TLR2 agonist conjugated to a solubilizing agent.

18. The method according to claim 1, wherein the soluble TLR2 moiety comprises an antigen that cannot raise a specific immune response to the one or more infectious agents.

19. The method according to claim 8, wherein R4Pam2Cys has the structure:

20. The method according to claim 5, wherein H4Pam2Cys has the structure:
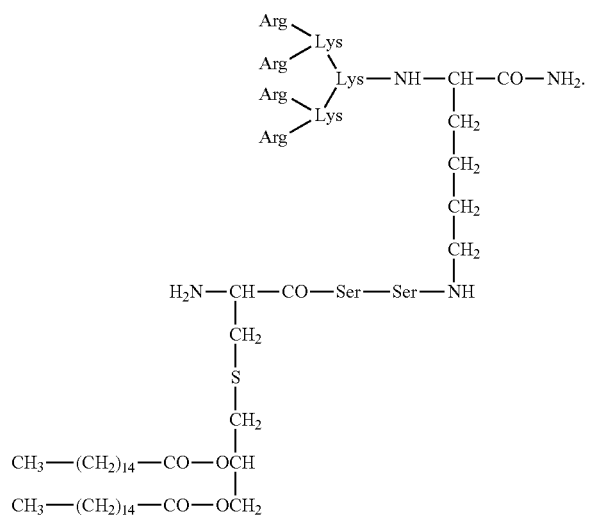
21. The method according to claim 11, wherein H8Pam2Cys has the structure:
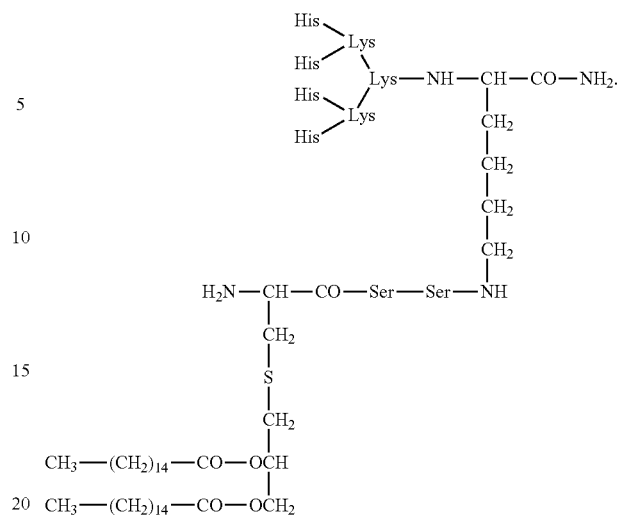
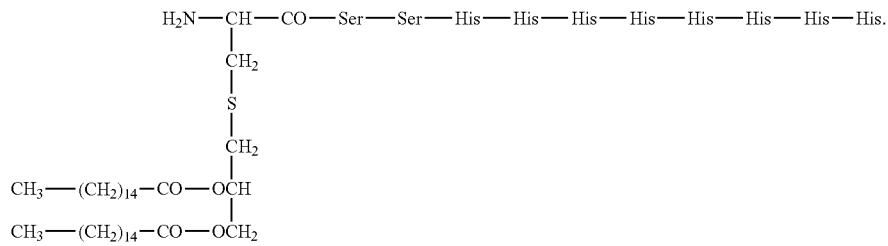
22. The method according to claim 10, wherein E8Pam2Cys has the structure:
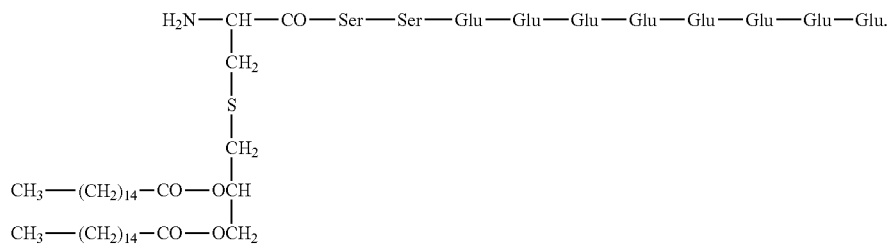

23. The method according to claim 5, wherein branched E8Pam2Cys has the structure:

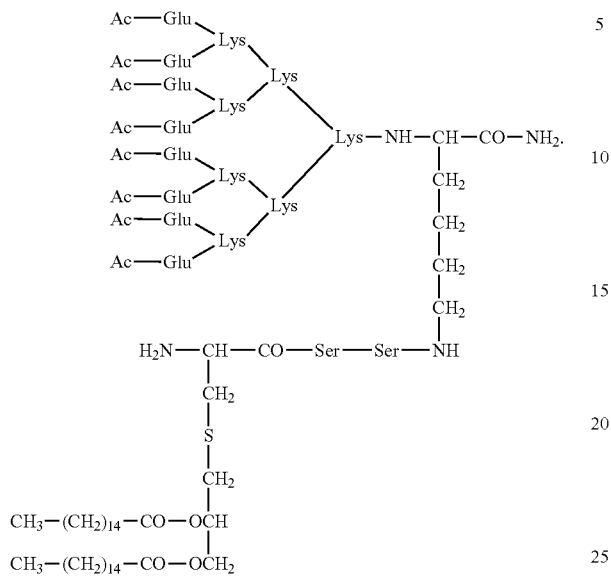

24. The method according to claim 7, wherein the soluble TLR2 moiety comprises polyethyleneglycol (PEG) and R4.

25. The method according to claim 24, wherein R4 is present as R4Pam2Cys.

26. The method according to claim 25, wherein R4Pam2Cys has the structure:

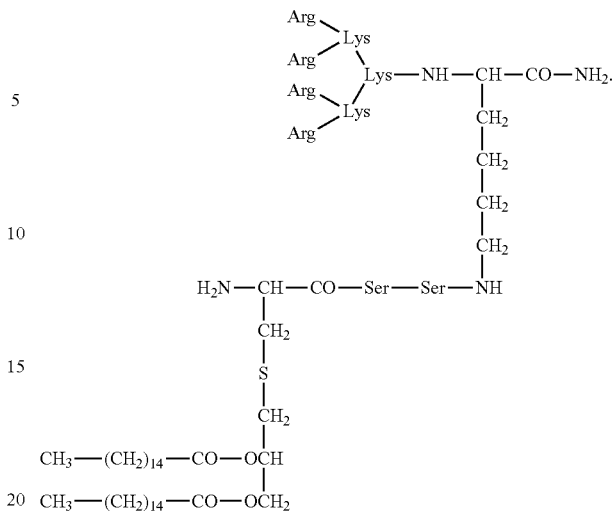

27. The method according to claim 1, wherein the subject has already been infected by the one or more viral infectious agents at the time of said administering, and wherein said administering treats the respiratory condition in the subject.

28. The method according to claim 1, wherein the subject has not yet been infected by the one or more viral infectious agents at the time of said administering, and wherein said administering prevents the respiratory condition in the subject.

* * * * *

UNITED STATES PATENT AND TRADEMARK OFFICE
CERTIFICATE OF CORRECTION

PATENT NO. : 9,676,819 B2
APPLICATION NO. : 13/825679
DATED : June 13, 2017
INVENTOR(S) : David Charles Jackson, Amabel Tan and Weiguang Zeng Page 1 of 2

It is certified that error appears in the above-identified patent and that said Letters Patent is hereby corrected as shown below:

Column 2,
Lines 25-26, "two scenes" should read --two serines--.

Column 4,
Line 59, "by (p<0.05)" should read --by * (p<0.05)--.

Column 5,
Line 30, "In humans. TLR2" should read --In humans, TLR2--.

Column 6,
Lines 47-48, "S-(2, 3-bis (stearoyloxy) propyl] cysteine or distearoyl-5-glyceryl-cysteine" should read --S-[2, 3-bis (stearoyloxy) propyl] cysteine or distearoyl-S-glyceryl-cystein--.

Column 14,
Line 56, "HHD nude and" should read --HHD male and--.

Column 15,
Line 23, "the HINT" should read --the H1N1--.
Line 48, "Edcnborough" should read --Edenborough--.
Line 52, "Medine" should read --Madine--.

Column 16,
Line 41, "CD11c $^{int/lo}$), F4/80$^+$" should read --CD11c $^{int/lo}$, F4/80$^+$--.
Line 45, "at 1μs/ml" should read --at 1μg/ml--.

Column 17,
Line 10, "cytometry. Intranasal" should read --cytometry.
                                              Intranasal--.

Signed and Sealed this
Twenty-fifth Day of September, 2018

Andrei Iancu
*Director of the United States Patent and Trademark Office*

CERTIFICATE OF CORRECTION (continued)

Column 18,
Line 24, "MID mice" should read --HHD mice--.
Line 38, "$PA_{224-233}$)" should read --$PA_{224-233}$,--.
Line 39, "UV-specific" should read --IAV-specific--.
Lines 45-46, "pattern of T cell" should read --pattern of $CD8^+$ T cell--.
Line 61, "that the we T cell" should read --that the $CD8^+$ T cell--.
Line 67, "virus. PR8. Both" should read --virus, PR8. Both--.

Column 19,
Line 47, "MCP-1, TNF-α and IL-12p70" should read --MCP-1, IFN-γ, TNF-α and IL-12p70--.

Column 21,
Line 57, "*Hum Immunol* 61:438-52," should read --*Hum Immunol* 61:438-52.--.

Column 22,
Line 35, "TLR2moiety" should read --TLR2 moiety--.
Line 39, "TLR2moiety" should read --TLR2 moiety--.